(12) United States Patent
Nishimura et al.

(10) Patent No.: US 9,676,576 B2
(45) Date of Patent: *Jun. 13, 2017

(54) SHEET DISCRIMINATOR AND IMAGE FORMING APPARATUS INCORPORATING SAME

(71) Applicants: Takayuki Nishimura, Kanagawa (JP); Tetsuya Ofuchi, Kanagawa (JP); Tohru Matsumoto, Ibaraki (JP); Yukifumi Kobayashi, Kanagawa (JP)

(72) Inventors: Takayuki Nishimura, Kanagawa (JP); Tetsuya Ofuchi, Kanagawa (JP); Tohru Matsumoto, Ibaraki (JP); Yukifumi Kobayashi, Kanagawa (JP)

(73) Assignee: RICOH COMPANY, LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/096,730

(22) Filed: Apr. 12, 2016

(65) Prior Publication Data

US 2016/0221780 A1 Aug. 4, 2016

Related U.S. Application Data

(63) Continuation of application No. 14/582,261, filed on Dec. 24, 2014, now Pat. No. 9,346,291.

(30) Foreign Application Priority Data

Dec. 26, 2013 (JP) .................................. 2013-268958

(51) Int. Cl.
*H04N 1/04* (2006.01)
*B65H 7/20* (2006.01)
(Continued)

(52) U.S. Cl.
CPC .............. *B65H 7/20* (2013.01); *B41J 11/009* (2013.01); *B65H 1/04* (2013.01); *B65H 7/14* (2013.01);
(Continued)

(58) Field of Classification Search
CPC ........ B65H 7/20; B65H 7/14; G01N 21/4738; G01N 21/55
(Continued)

(56) References Cited

U.S. PATENT DOCUMENTS 5,689,757 A * 11/1997 Ferrante ................. G01N 21/86
356/446
6,477,892 B1 11/2002 Lindig
(Continued)

FOREIGN PATENT DOCUMENTS

JP 7-175955 7/1995
JP 2005-070508 A 3/2005
(Continued)

*Primary Examiner* — Houshang Safaipour
(74) *Attorney, Agent, or Firm* — Harness, Dickey & Pierce, PLC

(57) ABSTRACT

A sheet discriminator includes a sheet loader on which a recording medium is loaded, an information detector to detect information of the recording medium loaded on the sheet loader, and a sheet distinguisher to distinguish a type of the recording medium based on the information detected by the information detector. The information detector detects the information of the recording medium with the recording medium being inserted between the sheet loader and the information detector. An image forming apparatus incorporates the sheet discriminator and an image forming part to form an image on the recording medium.

20 Claims, 20 Drawing Sheets

(51) Int. Cl.
*B41J 11/00* (2006.01)
*B65H 1/04* (2006.01)
*B65H 7/14* (2006.01)
*G01N 21/47* (2006.01)
*G01N 21/55* (2014.01)
*G03G 15/00* (2006.01)

(52) U.S. Cl.
CPC ......... *G01N 21/4738* (2013.01); *G01N 21/55* (2013.01); *G03G 15/6594* (2013.01); *B65H 2511/13* (2013.01); *B65H 2553/41* (2013.01); *G01N 2021/4764* (2013.01)

(58) Field of Classification Search
USPC .................................. 358/1.9, 474, 498, 497
See application file for complete search history.

(56) References Cited

U.S. PATENT DOCUMENTS

| | | | |
|---|---|---|---|
| 6,718,145 B2 * | 4/2004 | Ohta | G03G 15/5029 399/16 |
| 9,346,291 B2 * | 5/2016 | Nishimura | B65H 1/04 |
| 2005/0078973 A1 | 4/2005 | Suzuki | |
| 2012/0134693 A1 | 5/2012 | Hoshi et al. | |
| 2013/0057861 A1 | 3/2013 | Ishii et al. | |
| 2013/0057868 A1 | 3/2013 | Oba et al. | |
| 2013/0194573 A1 | 8/2013 | Ohba et al. | |
| 2013/0216245 A1 | 8/2013 | Hoshi et al. | |
| 2013/0216246 A1 | 8/2013 | Hoshi et al. | |
| 2013/0216247 A1 | 8/2013 | Oba et al. | |
| 2013/0228674 A1 | 9/2013 | Oba et al. | |
| 2013/0235377 A1 | 9/2013 | Ishii et al. | |
| 2014/0241742 A1 | 8/2014 | Hoshi et al. | |
| 2014/0268151 A1 | 9/2014 | Ohba et al. | |

FOREIGN PATENT DOCUMENTS

| | | |
|---|---|---|
| JP | 2006-201560 A | 8/2006 |
| JP | 2007-233186 A | 9/2007 |
| JP | 2010-262569 A | 11/2010 |
| JP | 2012-208103 A | 10/2012 |

* cited by examiner

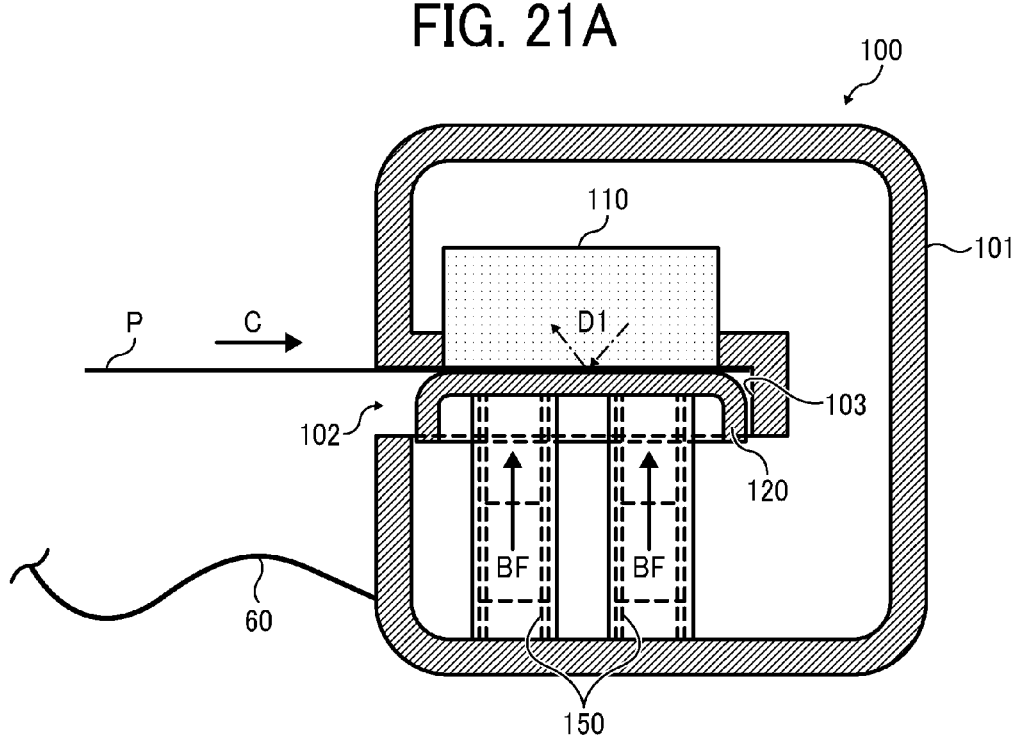
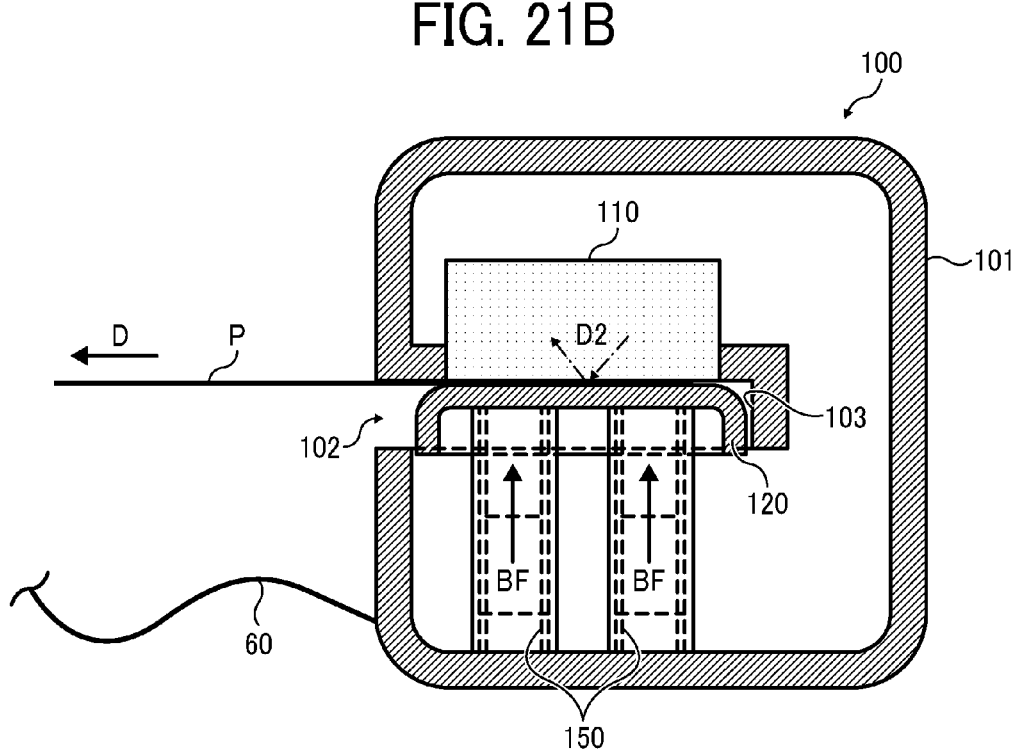

SHEET DISCRIMINATOR AND IMAGE FORMING APPARATUS INCORPORATING SAME

CROSS-REFERENCE TO RELATED APPLICATIONS

This patent application is a continuation application of U.S. application Ser. No. 14/582,261 filed on Dec. 24, 2014, and claims priority pursuant to 35 U.S.C. §119(a) to Japanese Patent Application No. 2013-268958, filed on Dec. 26, 2013, in the Japan Patent Office, the entire disclosure of which is hereby incorporated by reference herein.

BACKGROUND

Technical Field

This disclosure relates to a sheet discriminator to discriminate sheet types and an image forming apparatus including the sheet discriminator.

Related Art

In known image forming processes, to achieve higher printing quality, an image forming apparatus automatically discriminates sheet types and sets image forming conditions according to the detected sheet type.

An example of an image forming apparatus shows a configuration in which a sheet discriminator is disposed inside the image forming apparatus to discriminate information of a sheet being conveyed in a sheet conveying path.

This sheet discriminator includes an optical sensor that functions as an information detector to detect information of the sheet and that has a light emitting element and a light receiving element therein. The sheet discriminator causes the light emitting element of the optical sensor to emit light and the light receiving element of the optical sensor to receive the light reflected on a surface of the sheet traveling in the sheet conveying path, and detects sheet information based on optical information including a light amount of the received light.

Accordingly, based on the sheet information thus detected by the optical sensor, a controller that functions as a sheet distinguisher to distinguish the sheet types, the image forming apparatus sets the image forming conditions according to the sheet type.

SUMMARY

At least one aspect of this disclosure provides a sheet discriminator including a sheet loader on which a recording medium is loaded, an information detector to detect information of the recording medium loaded on the sheet loader, and a sheet distinguisher to distinguish a type of the recording medium based on the information detected by the information detector. The information detector detects the information of the recording medium with the recording medium being inserted between the sheet loader and the information detector.

Further, at least one aspect of this disclosure provides an image forming apparatus including the above-identified sheet discriminator and an image forming part to form an image on the recording medium.

BRIEF DESCRIPTION OF THE SEVERAL VIEWS OF THE DRAWINGS

FIG. 21A is a cross sectional view illustrating a sheet discriminator according to another example of this disclosure, when the sheet is inserted into an opening;

FIG. 21B is a cross sectional view illustrating the sheet discriminator of FIG. 21A when the sheet is pulled out from the opening of the sheet discriminator;

DETAILED DESCRIPTION

Figure 1:
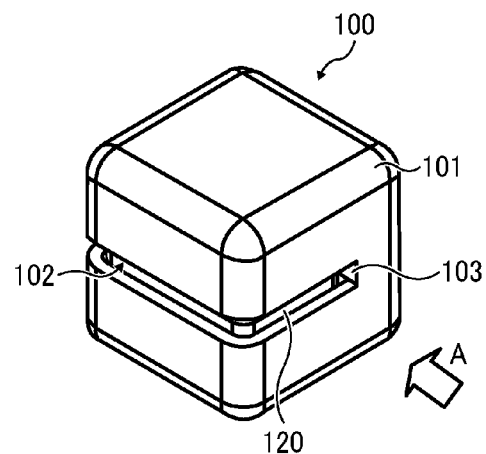
FIG. 1 is a diagram illustrating a sheet discriminator according to an example of this disclosure.

It will be understood that if an element or layer is referred to as being "on", "against", "connected to" or "coupled to" another element or layer, then it can be directly on, against, connected or coupled to the other element or layer, or intervening elements or layers may be present. In contrast, if an element is referred to as being "directly on", "directly connected to" or "directly coupled to" another element or layer, then there are no intervening elements or layers present. Like numbers referred to like elements throughout. As used herein, the term "and/or" includes any and all combinations of one or more of the associated listed items.

Spatially relative terms, such as "beneath", "below", "lower", "above", "upper" and the like may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements describes as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors herein interpreted accordingly.

Although the terms first, second, etc. may be used herein to describe various elements, components, regions, layers and/or sections, it should be understood that these elements, components, regions, layer and/or sections should not be limited by these terms. These terms are used to distinguish one element, component, region, layer or section from another region, layer or section. Thus, a first element, component, region, layer or section discussed below could be termed a second element, component, region, layer or section without departing from the teachings of the present disclosure.

The terminology used herein is for describing particular embodiments and examples and is not intended to be limiting of exemplary embodiments of this disclosure. As used herein, the singular forms "a", "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

Descriptions are given, with reference to the accompanying drawings, of examples, exemplary embodiments, modification of exemplary embodiments, etc., of an image forming apparatus according to exemplary embodiments of this disclosure. Elements having the same functions and shapes are denoted by the same reference numerals throughout the specification and redundant descriptions are omitted. Elements that do not demand descriptions may be omitted from the drawings as a matter of convenience. Reference numerals of elements extracted from the patent publications are in parentheses so as to be distinguished from those of exemplary embodiments of this disclosure.

This disclosure is applicable to any image forming apparatus, and is implemented in the most effective manner in an electrophotographic image forming apparatus.

In describing preferred embodiments illustrated in the drawings, specific terminology is employed for the sake of clarity. However, the disclosure of this disclosure is not intended to be limited to the specific terminology so selected and it is to be understood that each specific element includes any and all technical equivalents that have the same function, operate in a similar manner, and achieve a similar result.

Referring now to the drawings, wherein like reference numerals designate identical or corresponding parts throughout the several views, preferred embodiments of this disclosure are described.

Now, a description is given of a sheet discriminator 100 according to this disclosure with reference to FIGS. 1 through 28.

FIG. 1 is a diagram illustrating a sheet discriminator according to an example of this disclosure.

It is to be noted in the following examples that the term "sheet" is not limited to indicate a paper material but also includes OHP (overhead projector) transparencies, OHP film sheets, coated sheet, thick paper such as post card, thread, fiber, fabric, leather, metal, plastic, glass, wood, and/or ceramic by attracting developer or ink thereto, and is used as a general term of a recorded medium, recording medium, sheet member, and recording material to which the developer or ink is attracted.

The sheet discriminator 100 includes an external case 101 that functions as a housing body. The external case 101 includes a sheet information detecting sensor 110 and a sheet loading table 120 therein. The sheet information detecting sensor 110 functions as an information detector to detect information to be used to discriminate the sheet P. The sheet loading table 120 functions as a sheet loader on which the sheet P is located.

Figure 4:
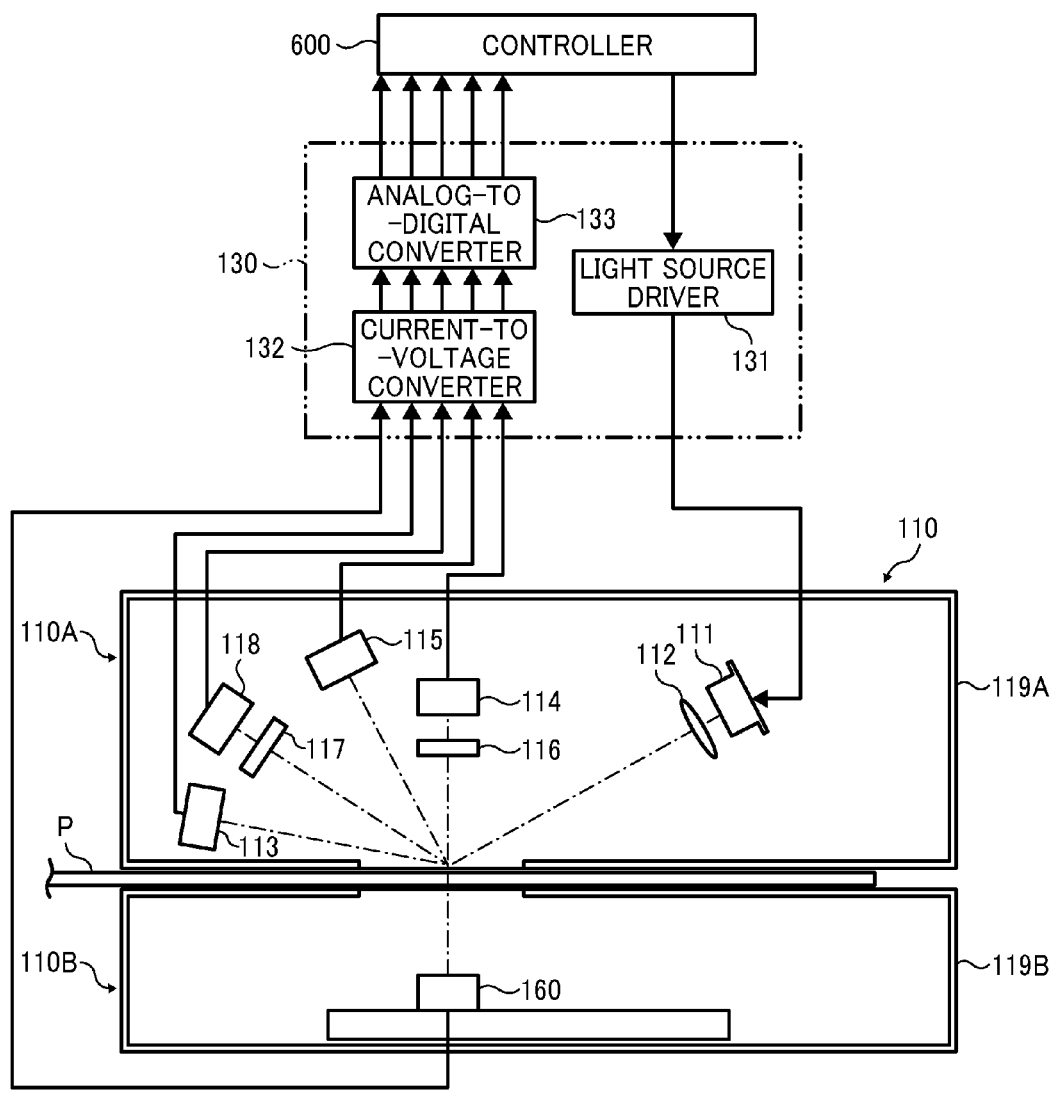
FIG. 4 is a diagram illustrating a configuration of an optical sensor and a processing device.
Figure 5:
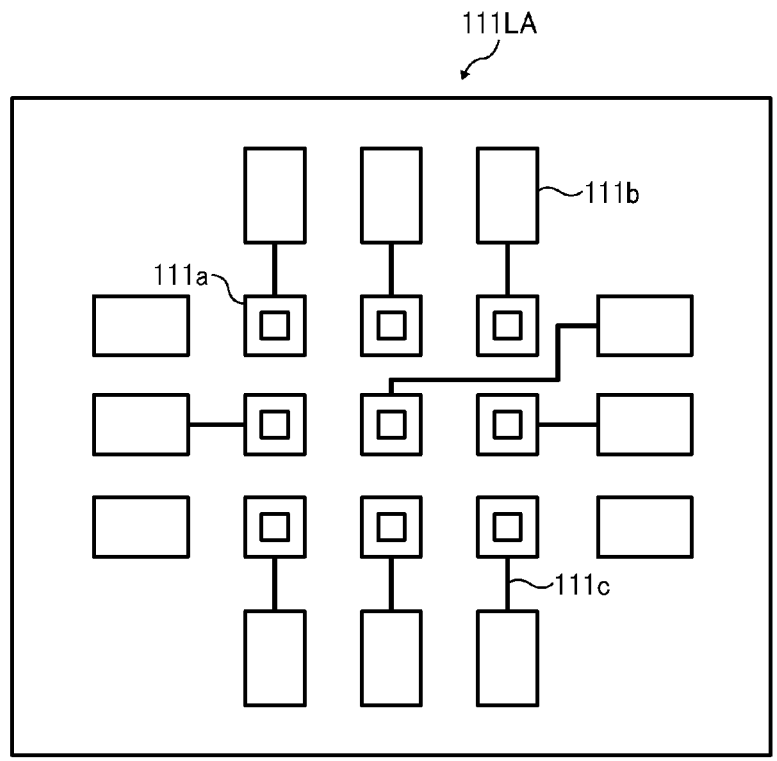
FIG. 5 is a diagram illustrating a structure of a vertical cavity surface emitting laser array (a VCSEL array)

It is to be noted that the sheet information detecting sensor 110 is connected to a controller 600 that functions as a sheet distinguisher (see FIG. 4). The controller 600 controls start and stop of light emission of a light source 111 (see FIG. 4) of the sheet information detecting sensor 110 via a light emission processing unit 130 (see FIG. 4) that functions as a light emission controller.

The external case 101 has sidewalls. An opening 102 is formed on one of the sidewalls of the external case 101. The sheet P is inserted into and removed from the opening 102 so that the sheet P is loaded on the sheet loading table 120.

Figures 2A, 2B:
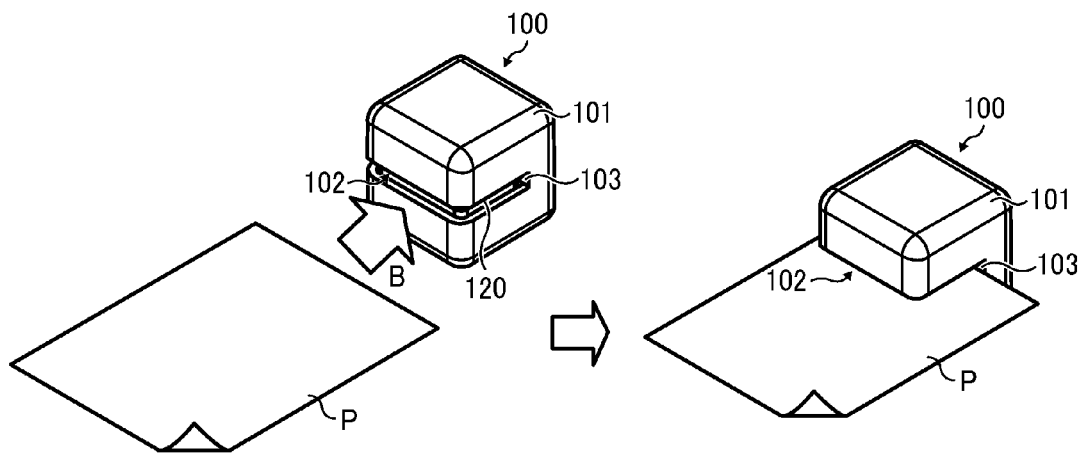
FIG. 2A is a perspective view illustrating the sheet discriminator when a sheet is being inserted thereto through an opening.
FIG. 2B is a perspective view illustrating the sheet discriminator when the sheet approaches or contacts an end face of the opening of the sheet discriminator.

The sheet P is inserted into the opening 102 of the sheet discriminator 100 in a direction indicated by arrow B as illustrated in FIG. 2A and pushed further until the sheet P contacts an end face 103 of the opening 102 or approaches the end face 103 as illustrated in FIG. 2B.

At this time, it is preferable that an operator grips both left and right ends of the sheet P by hands with respect to the direction B and inserts the sheet P while checking that the sheet P has no deformation such as wrinkle or crease on the sheet P. It is to be noted that sheet insertion to the opening 102 is not limited to the above-described way but is applicable with any way of sheet insertion as long as the sheet P can be inserted into the opening 102 of the sheet discriminator 100 horizontally.

To discriminate a type of the sheet P, the operator inserts the sheet P into the external case 101 via the opening 102 while checking that there is no deformation such as curls on the sheet P. Then, the operator loads the sheet P on the sheet loading table 120, so that the sheet information detecting sensor 110 detects information of the sheet P while the sheet P is loaded on the sheet loading table 120.

In a comparative sheet discriminator, when a light emitting element of an optical sensor emits light to a deformed portion of a sheet having deformation such as curl and waveform induced when the sheet is being conveyed, optical information received by the light receiving element varies according to the state of deformation. Therefore, it is likely that correct sheet information is not detected and accuracy in sheet discrimination is degraded.

By contrast, with the configuration the sheet discriminator 100, the sheet information detecting sensor 110 does not detect deformed portions on the sheet P and detects correct sheet information, and therefore performance of precise discrimination of sheet types is prevented from being degraded.

Figure 3A:
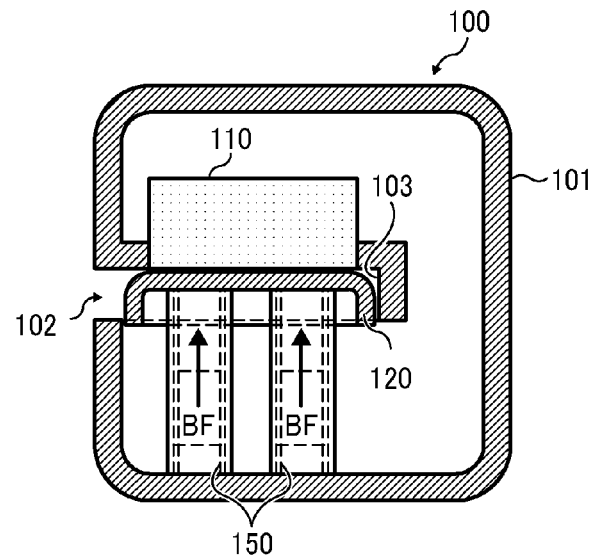
FIG. 3A is a cross sectional view illustrating the sheet discriminator when no sheet is inserted in the opening of the sheet discriminator.
Figure 3B:
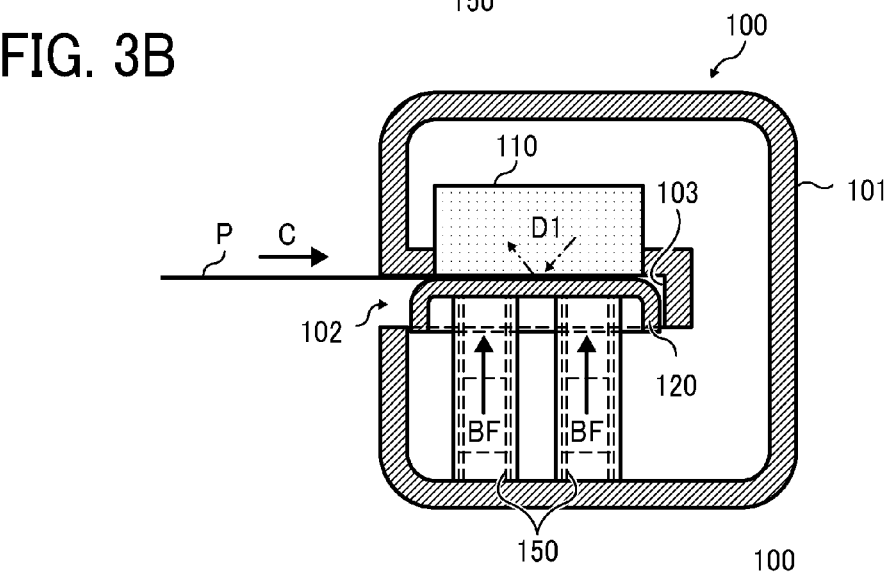
FIG. 3B is a cross sectional view illustrating the sheet discriminator when the sheet is inserted into the opening and remains therein.
Figure 3C:
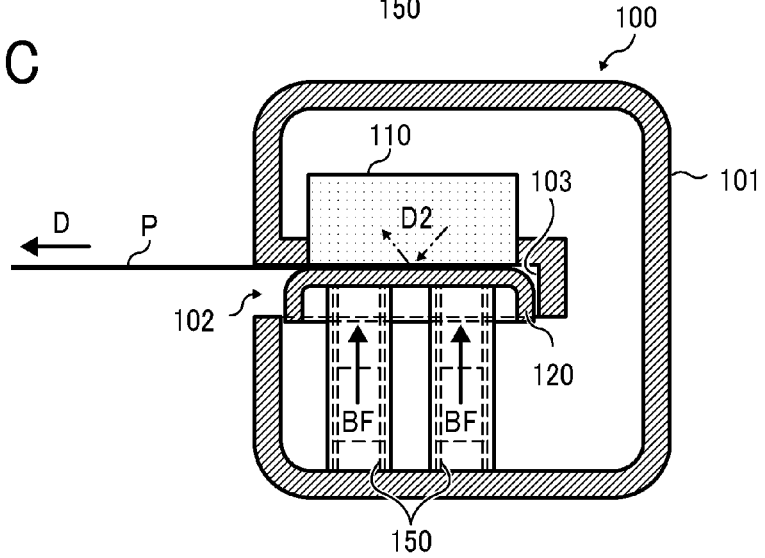
FIG. 3C is a cross sectional view illustrating the sheet discriminator when the sheet is being pulled out from the opening.

FIGS. 3A through 3C are cross sectional views illustrating the sheet discriminator 100 as viewed from arrow A illustrated in FIG. 1.

Specifically, FIG. 3A is a cross sectional view illustrating the sheet discriminator 100 when no sheet P is inserted in the opening 102 of the sheet discriminator 100.

FIG. 3B is a cross sectional view illustrating the sheet discriminator 100 when the sheet P is inserted into the opening 102 and remains therein.

FIG. 3C is a cross sectional view illustrating the sheet discriminator 100 when the sheet P is being pulled out from the opening 102.

As illustrated in FIG. 3A, the sheet loading table 120 is located at a position facing the sheet information detecting sensor 110 with a given gap at a lower part inside the external case of the sheet discriminator 100.

Biasing members 150 such as spring are disposed facing the sheet information detecting sensor 110 with the sheet loading table 120 interposed therebetween. The sheet loading table 120 is biased by the biasing members 150 in a direction indicated by arrows BF in FIG. 3A, that is, toward the sheet information detecting sensor 110.

As illustrated in FIG. 4, the sheet information detecting sensor 110 includes a light source 111, a collimator lens 112, receivers 113, 114, 115, and 118, polarizing filters 116 and 117, and dark boxes (camera obscuras) 119A and 119B to accommodate these optical units therein.

Each of the dark boxes 119A and 119B is a metal box such as an aluminum box, and anodic oxide coating with black dye on a surface thereof in order to reduce the impact of ambient light and stray light.

The light source 111 functions as a light emitter and includes multiple light emitting elements 111a, which are vertical cavity surface emitting laser (VCSEL). Specifically, the light source 111 includes a VCSEL array 111LA.

As illustrated in FIG. 4, the light source 111 of the sheet information detecting sensor 110 includes a 2 dimensional array with nine (9) light emitting elements 111a. The VCSEL array 111LA includes electrode pads 111b and wiring members 111c. Each wiring member 111c connects one of the multiple light emitting elements 111a with a corresponding one of the electrode pads 111b.

Figure 6:
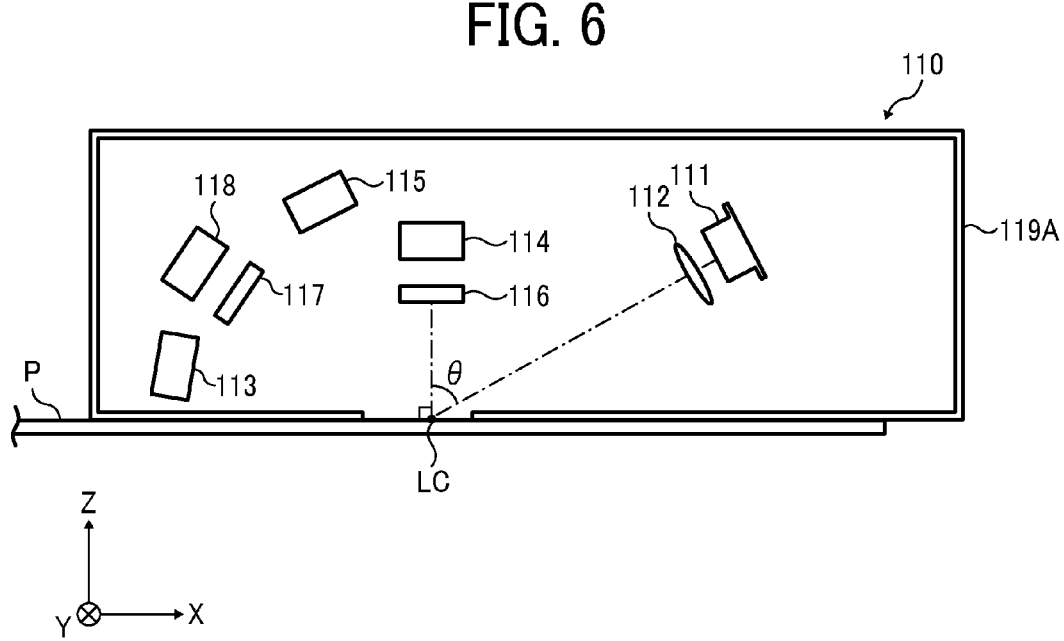
FIG. 6 is a diagram illustrating an incident angle of an irradiation light to the sheet.

The light source 111 is disposed such that linearly polarized light of S-polarized light to the sheet P is emitted. As illustrated in FIG. 6, an incidence angle 9 of light from the light source 111 to the sheet P is 80 degrees. The light emission processing unit 130 turns on/off the light source 111.

The collimator lens 112 is disposed on a light path of light emitted from the light source 111 to make the light substantially parallel, which is hereinafter referred to as a substantially parallel light. The substantially parallel light has passes through the collimator lens 112 then through an opening provided on the dark box 119A, and emits the light to the sheet P. It is to be noted that a center of a light emission region on a surface of the sheet P is hereinafter referred to as a "center of light emission LC" and the light passed through the collimator lens 112 is also referred to as an "irradiation light".

When the light enters onto a border surface of a medium, a surface that contains an incident light (an incoming radiation) and a normal line of a border surface standing at a light incident point. When the incident light includes multiple light beams, each light beam has the plane of incidence. Here, for convenience, the plane of incidence of light incoming to the center of light emission LC is referred to as a plane of incidence of the sheet P. Specifically, the plane of incidence of a sheet contains the center of light emission LC and is parallel to X and Z surfaces of the sheet P.

It is to be noted that terms "S-polarized light" and "P-polarized light" are used for not only the incident light to the sheet P but also a reflection light on the sheet P based on a polarization direction of the incident light to the sheet P for easy understanding of this technique. On the plane of incidence, a polarization direction identical to the incident light is referred to as "S-polarized light" and a polarization direction perpendicular to the incident light is referred to as "P-polarized light".

The polarizing filter 116 is disposed on a +Z side of the center of light emission LC. The polarizing filter 116 is a polarizing filter that transmits the P-polarized light and blocks or reflects the S-polarized light. It is to be noted that a polarizing beam splitter that has the same functions as the polarizing filter 116 can be employed instead of the polarizing filter 116.

Figure 7:
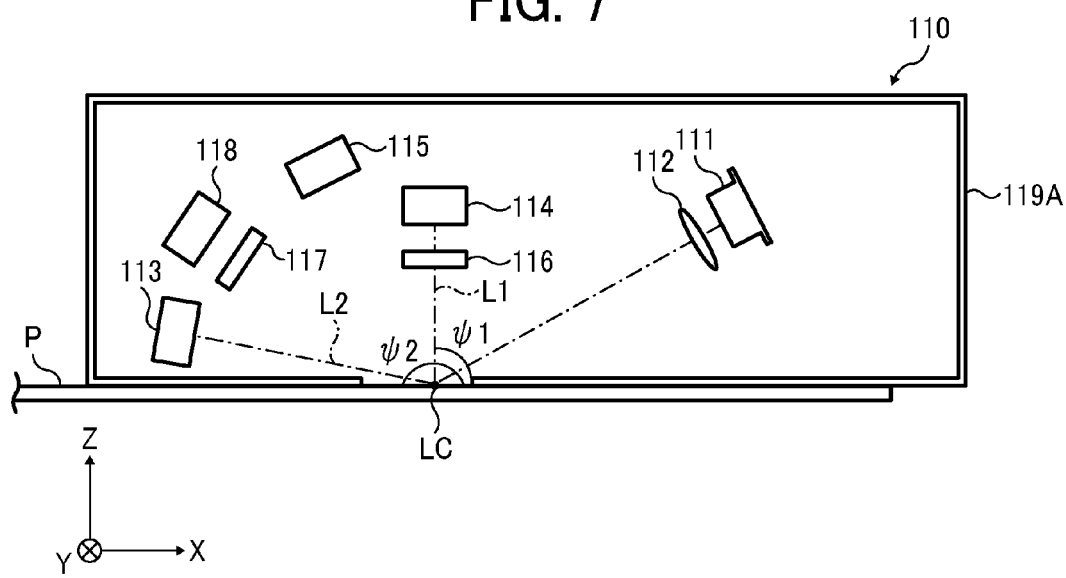
FIG. 7 is a diagram illustrating respective positions of receivers.

The receiver 114 is disposed on the +Z side of the polarizing filter 116 and functions as a light receiver to receive the light transmitted through the polarizing filter 116. As illustrated in FIG. 7, a line L1 connects the center of light emission LC, a center of the polarizing filter 116, and a center of the receiver 114. The line L1 and the surface of the sheet P form an angle ψ1 of 90 degrees.

The receiver 113 is disposed on the +X side of the center of light emission LC with respect to an X axis. As illustrated in FIG. 7, a line L2 connects the center of light emission LC and a center of the receiver 113. The line L2 and the surface of the sheet P form an angle ψ2 of 170 degrees.

A center of the light source 111, the center of light emission LC, the center of the polarizing filter 116, and respective centers of the receivers 113, 114, 115, and 118 fall on the substantially identical vertical plane.

The reflection light reflected on the sheet P when the sheet P is irradiated can be separated to reflection light reflected on the surface of the sheet P and reflection light reflected from an inside of the sheet P. Further, the reflection light reflected on the surface of the sheet P can be separated to specular reflection light (SRL) and diffused reflection light (DRL).

Figure 8A:
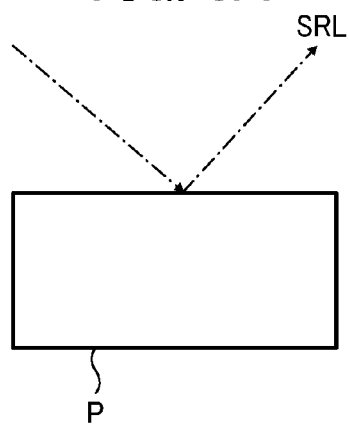
FIG. 8A is a diagram illustrating a surface specular reflection light.
Figure 8B:
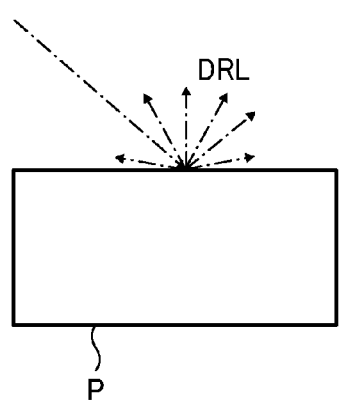
FIG. 8B is a diagram illustrating a surface diffused reflection light.
Figure 8C:
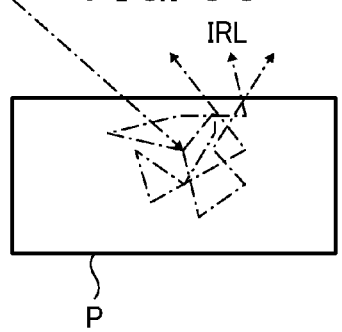
FIG. 8C is a diagram illustrating an internal reflection light.

For convenience, the specular reflection light reflected on the surface of the sheet P is hereinafter referred to as a "surface specular reflection light" (see FIG. 8A) and the diffused reflection light reflected on the surface of the sheet P is hereinafter referred to as a "surface diffused reflection light" (see FIG. 8B).

The surface of the sheet P includes plane portions and sloped portions. Based on a rate of the plane portions and the sloped portions, smoothness of the surface of the sheet P is determined. The light reflected on the plane portions becomes the surface specular reflection light and the light reflected on the sloped portions becomes the surface diffused reflection light. The surface diffused reflection light is the light fully reflected from an object (i.e., the sheet P) and a reflection direction has isotropy. As smoothness increases, the level of the surface specular reflection light rises.

By contrast, when the sheet P is a regular printing sheet, the reflection light reflected from the inside of the sheet P scatters in the fibers of the sheet P. Therefore, the reflection light is the diffused reflection light because the light scatters multiply in the sheet P. Hereinafter, for convenience, the reflection light reflected from the inside of the sheet P is also referred to as an "internal reflection light (IRL)" (see FIG. 8C). Similar to the surface diffused reflection light, the internal reflection light is the light fully reflected from an object (i.e., the sheet P) and the reflection direction is isotropic.

The polarization direction of the surface specular reflection light and the surface diffused reflection light toward the receiver (i.e., the receiver 114) is the same as the polarization direction of the incident light.

In order to rotate the polarization direction on the surface of the sheet S, the incident light is reflected on the sloped surface that is slanted to the rotation of the polarization direction with respect to an incident direction. Here, since the center of the light source (i.e., the light source 111), the center of light emission LC, and the center of each receiver (i.e., the receivers 113 and 114) fall on the same plane, the reflection light in the polarization direction rotated on the surface of the sheet P is not reflected in any direction of the receiver.

By contrast, the polarization direction of the internal reflection light is rotated with respect to the polarization direction of the incident light. It is thought that the light entered into the inside of the sheet (i.e., the sheet P) passes through the fibers of the sheet and optically rotates during multiple scattering in the sheet, and as a result, the polarization direction rotates.

Figure 9:
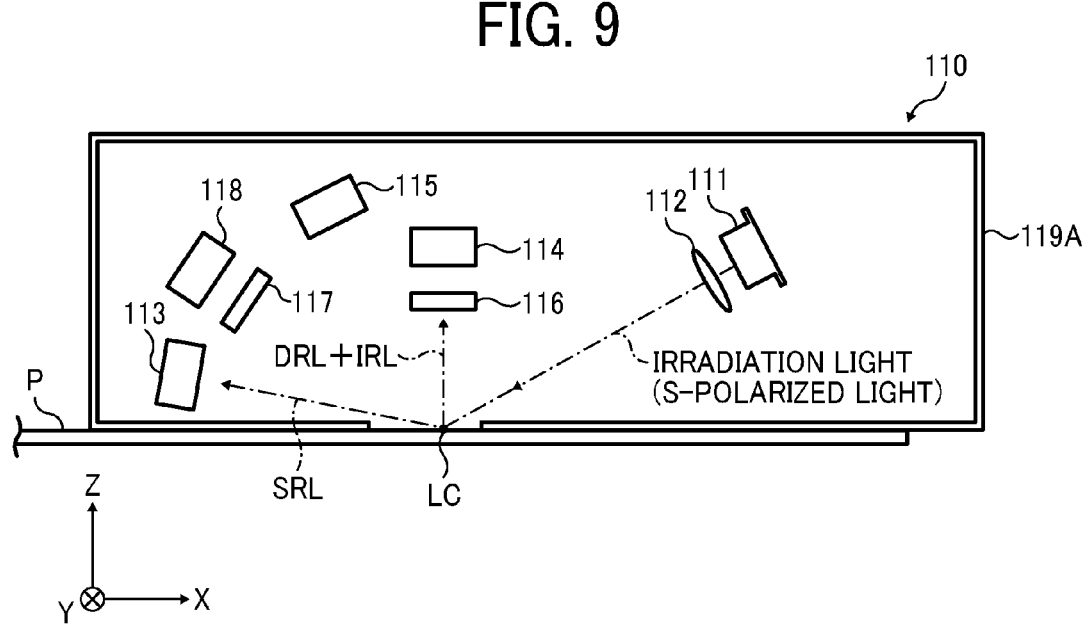
FIG. 9 is a diagram illustrating the light received by receivers.
Figure 10:
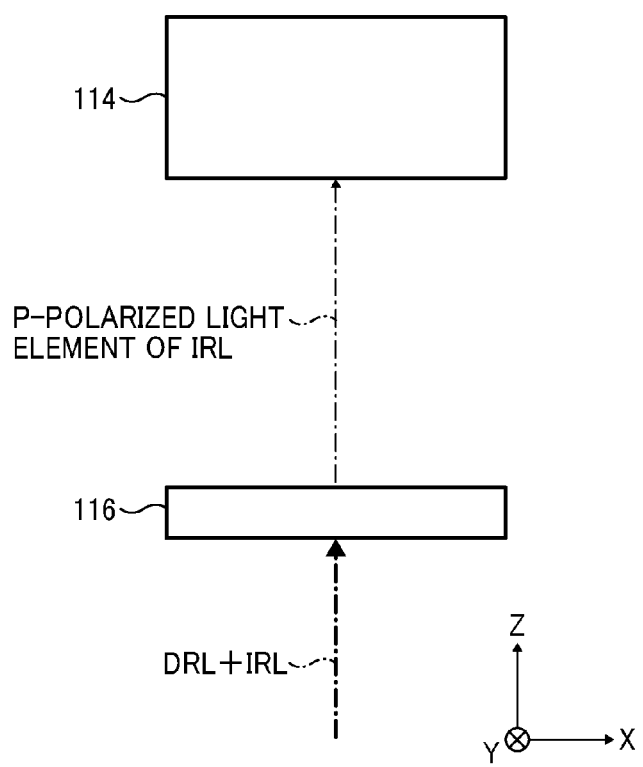
FIG. 10 is a diagram illustrating an incident light to a diffusion filter.

The reflection light including the surface diffused reflection light and the internal reflection light enters into the polarizing filter 116, as illustrated in FIG. 9.

Since the surface diffused reflection light is the S-polarized light that is the same as the incident light, the polarizing filter 116 blocks or reflects the surface diffused reflection light. By contrast, the internal reflection light includes both the S-polarized light and the P-polarized light, and therefore a component of the P-polarized light passes through the polarizing filter 116. Specifically, the component of the P-polarized light contained in the internal reflection light is received by the receiver 114 (see FIG. 10).

It is to be noted that the component of the P-polarized light included in the internal reflection light is also referred to as a "P-polarized light internal reflection light", for convenience. In addition, a component of the S-polarized light included in the internal reflection light is also referred to as an "S-polarized light internal reflection light".

The level of the P-polarized light internal reflection light has been proved to have a correlation to thickness and density of the sheet. It is because the level of the P-polarized light internal reflection light depends on a path length when the sheet passes through the fibers in the sheet P.

The receiver 113 receives reflection light having the surface specular reflection light, the surface diffused reflection light, and the internal reflection light. At this light receiving position, the level of the surface diffused reflection light and the level of the internal reflection light are significantly smaller than the level of the surface specular reflection light. Therefore, it is regarded as that the received light level of the receiver 113 substantially corresponds to the level of the surface specular reflection light (see FIG. 9).

Figure 11:
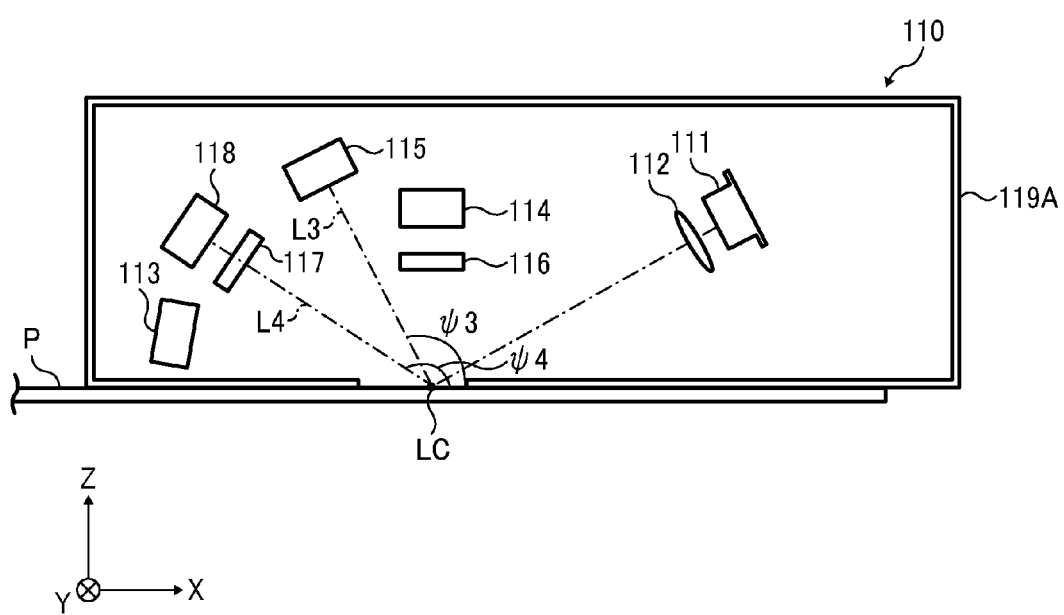
FIG. 11 is a diagram illustrating respective positions of different receivers.

The receiver 115 that functions as a light receiver is disposed at a position to receive the surface diffused reflection light and the internal reflection light. For example, as illustrated in FIG. 11, a line L3 connects the center of light emission LC and a center of the receiver 115. The line L3 and the surface of the sheet P form an angle ψ3 of 120 degrees. The center of the light source 111, the center of light emission LC, the center of the polarizing filter 116, and the respective centers of the receivers 113, 114, 115, and 118 fall on the substantially same vertical plane.

The polarizing filter 117 is disposed on the light path of the surface diffused reflection light and the internal reflection light. The polarizing filter 117 is a polarizing filter that transmits the P-polarized light and blocks or reflects the S-polarized light.

The receiver 118 is disposed on a light path of the light transmitted through the polarizing filter 117. The receiver 118 receives a component of the P-polarized light included in the internal reflection light.

For example, as illustrated in FIG. 11, a line L4 connects the center of light emission LC, a center of the polarizing filter 117, and a center of the receiver 118. The line L4 and the surface of the sheet P form an angle ψ4 of 150 degrees. The center of the light source 111, the center of light emission LC, the center of the polarizing filter 116, the center of the polarizing filter 117, and the respective centers of the receivers 113, 114, 115, and 118 fall on the substantially same vertical plane.

The receiver 160 illustrated in FIG. 4 functions as a transmitted light receiver and is disposed at a position to receive a light beam that is transmitted through the sheet P out of the light beams emitted from the light source 111 and irradiated to the sheet P.

The receivers 113, 114, 115, and 118 output respective electrical signals (electric current signals) corresponding to respective received light levels to the light emission processing unit 130.

As illustrated in FIG. 4, the light emission processing unit 130 includes a light source driver 131, a current-to-voltage converter 132, and an analog-to-digital (AD) converter 133. The light emission processing unit 130 is connected to the dark box 119A.

The light source driver 131 outputs the light source driving signal to the light source 111 according to instructions of the controller 600.

The current-to-voltage converter 132 converts electric current signals inputted by each receiver to voltage signals.

The AD converter 133 converts analog signals passing through the current-to-voltage converter 132 to digital signals and outputs the converted digital signals to the controller 600.

As described in this example, by including information obtained by the receiver 160 that receives a transmitted light in addition to information obtained by the receivers 113, 114, 115, and 118 receiving the reflection light, more precise discrimination of the type of the sheet P can be achieved. Accordingly, the sheet P can be discriminated based on information of the surface properties, thickness, and so forth.

A description is given of a control of sheet discrimination with reference to FIGS. 3A, 3B, 3C, and 12.

Figure 12:
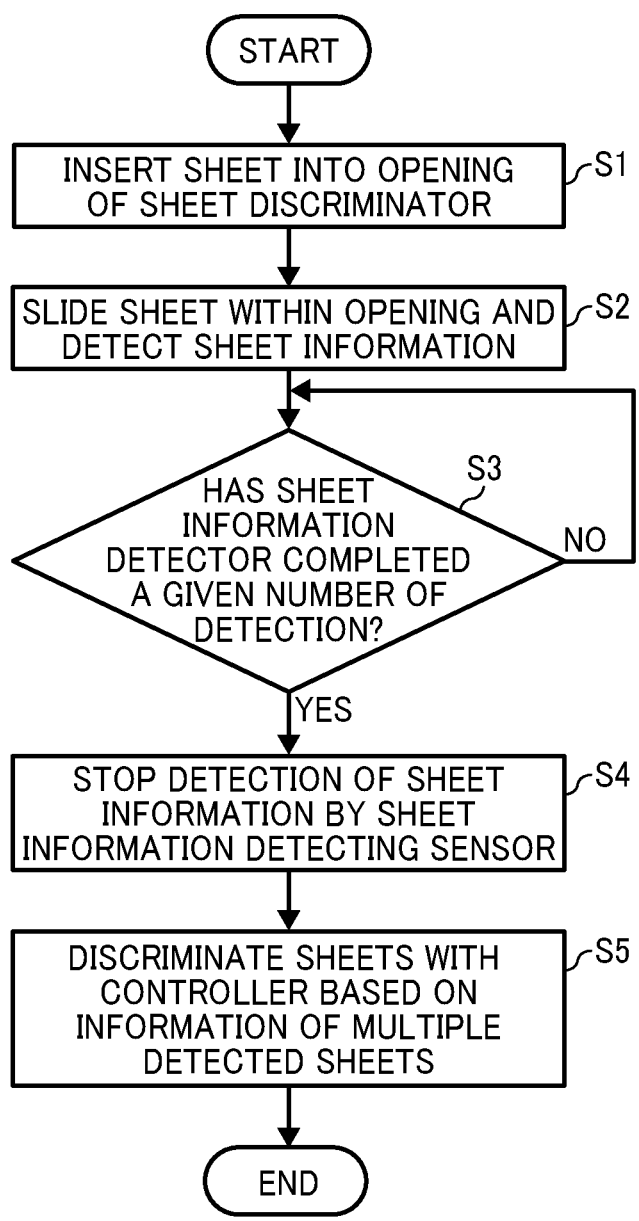
FIG. 12 is a flowchart illustrating an example of control of sheet discrimination performed by the sheet discriminator.

FIG. 12 is a flowchart illustrating an example of control of sheet discrimination performed by the sheet discriminator 100.

It is to be noted that the sheet information detecting sensor 110 detects information of the sheet P for multiple times at given detection intervals (sampling periods).

As illustrated in FIG. 3B, the sheet P is inserted toward the end face 103 of the opening 102 of the sheet discriminator 100 in the direction C, as described in step S1 in FIG. 12.

Then, the sheet information detecting sensor 110 performs a first information detection D1 in FIG. 3B with respect to the sheet P when the sheet P passes by the position facing the sheet information detecting sensor 110.

After the sheet P has reached the end face 103 of the opening 102, the sheet P is removed. When pulling out the sheet P from the opening 102, the sheet P moves in a direction indicated by arrow D in FIG. 3C. At this time, the sheet information detecting sensor 110 performs a second information detection D2 in FIG. 3C. Accordingly, the sheet information detecting sensor 110 detects the sheet P at different points on the sheet P in the first information detection and the second information detection.

As described above, the sheet discriminator 100 according to this example slides the sheet P in the opening 102 for multiple detections, as described in step S2 in the flowchart of FIG. 12. Based on the information obtained by the sheet information detecting sensor 110, the controller 600 discriminates the sheet P, as described in step S4 in FIG. 11.

Further, in the sheet discriminator 100 according to this example, an operator holding the sheet P inserts the sheet P into the opening 102 and slides the sheet P with respect to the external case 101. By simply so doing, information of multiple sheets P can be obtained, thereby enhancing sheet handling performance.

When the sheet information detecting sensor 110 detects the sheet P for given times (e.g., two times in this example), which is YES in step S3 in the flowchart of FIG. 12, the controller 600 causes the sheet information detecting sensor 110 to stop light emission, as described in step S4 in the flowchart of FIG. 12. Then, the controller 600 determines the sheet P based on the sheet information obtained from the multiple points on the sheet P, as described in step S5 in the flowchart of FIG. 12.

When the sheet information detecting sensor 110 does not complete information detection of the sheet P for the given times, which is NO in step S3 in the flowchart of FIG. 12, the procedure is repeated until the condition of step S3 is satisfied.

As described above, the controller 600 discriminates the sheet P based on the sheet information obtained from the multiple points on the sheet P. This operation encourages averaging discrimination results and obtaining the median value of the discrimination results, and therefore measurement errors such as noise can be reduced or prevented and more precise discrimination of the sheet P can be achieved.

It is to be noted that the controller 600 may discriminate the thickness, surface properties, and brand of the sheet P based on the detection results obtained by the sheet information detecting sensor 110.

Further, given detection intervals (sampling periods) of sheet information detected by the sheet information detecting sensor 110 may be optionally set and/or changed by a service representative or a user. By so doing, as the detection intervals of sheet information of the sheet P become shorter (as the sampling periods of sheet information of the sheet P are more accelerated), more detection results can be obtained at the same amount of movement of the sheet P in the opening 102. As a result, more precise discrimination of the sheet P can be performed.

Further, as illustrated in FIGS. 3A and 3B, the biasing member 150 biases and presses the sheet loading table 120 toward the sheet information detecting sensor 110. By so doing, a detection face of the sheet information detecting sensor 110 can contact or approach the sheet P. As a result, while reducing or preventing disturbances such as deformation of the sheet P and entry of ambient light, precise sheet discrimination can be performed.

Further, in FIGS. 3A and 3B, the sheet information detecting sensor 110 is disposed on the upper side of the sheet discriminator 100 and the sheet loading table 120 is disposed on the lower side with the sheet discriminator 100. In other words, the sheet information detecting sensor 110 and the sheet loading table 120 are disposed facing each other with the opening 102 interposed therebetween. Specifically, the sheet loading table 120 is disposed below the sheet information detecting sensor 110. However, the positional relation of the sheet information detecting sensor 110 and the sheet loading table 120 is not limited thereto as long as a distance between the detection face of the sheet information detecting sensor 110 and the sheet P is secured and the detection face of the sheet information detecting sensor 110 can contact the sheet P.

However, the configuration in which the sheet information detecting sensor 110 is disposed above the sheet loading table 120 and facing the sheet loading table 120 can avoid foreign materials brought into the sheet discriminator 100 via the sheet P and dust of the sheet P adhering and entering to the sheet information detecting sensor 110. Therefore, it is preferable that the sheet information detecting sensor 110 and the sheet loading table 120 have the positional relation as illustrated in FIGS. 3A and 3B. In other words, the sheet P and the sheet information detecting sensor 110 can be retained in a good positional relation. Therefore, information of the sheet P can be detected precisely.

Further, this configuration does not have any restriction in handling sheet discrimination. For example, no pressure is applied between the sheet information detecting sensor 110 and the sheet P, the sheet P is not deformed during a detecting operation, and a user does not have to apply any force when handling the sheet P. Therefore, information of the surface of the sheet P can be obtained easily.

It is to be noted that the sheet information detecting sensor 110 has at least a function to obtain information on the surface of the sheet P.

A light-emitting diode (LED) is generally employed as the light source 111 of the sheet information detecting sensor 110. By employing a surface emitting laser having VCSEL elements, surface information of the sheet P can be detected more precisely. Therefore, more precise detection results can be obtained.

Further, the sheet information detecting sensor 110 is preferably include at least a specular reflection light receiver (e.g., the receivers 113, 114, 115, and 118) to receive specular reflection light reflected on the sheet P and a diffused reflection light receiver (e.g., the receiver 113) to receive diffused reflection light reflected on the sheet P out of the light beams emitted from the light source 111 and irradiated to the sheet P. The sheet information detecting sensor 110 can be a known optical sensor.

Since the sheet information detecting sensor 110 has multiple sensors disposed at different angles to detect scattered light beams of diffused reflection light, more precise detection results of sheet information can be obtained than the information obtained from specular reflection light. As a result, more precise detection results of sheet information can be performed.

Figure 13A:
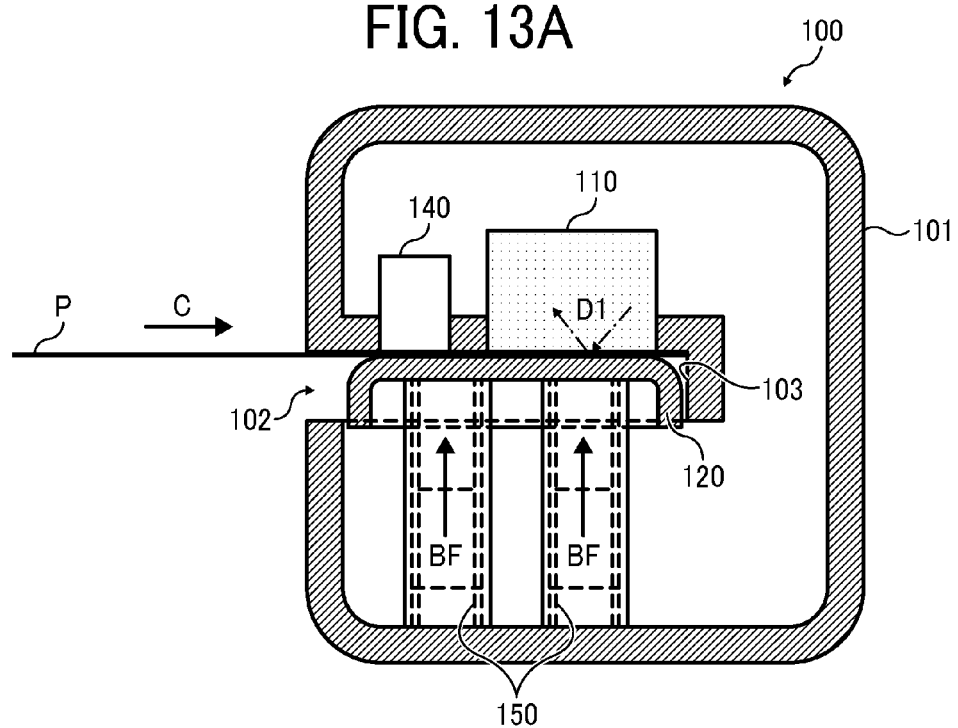
FIG. 13A is a cross sectional view illustrating a sheet discriminator according to another example of this disclosure, when the sheet is inserted into an opening.
Figure 13B:
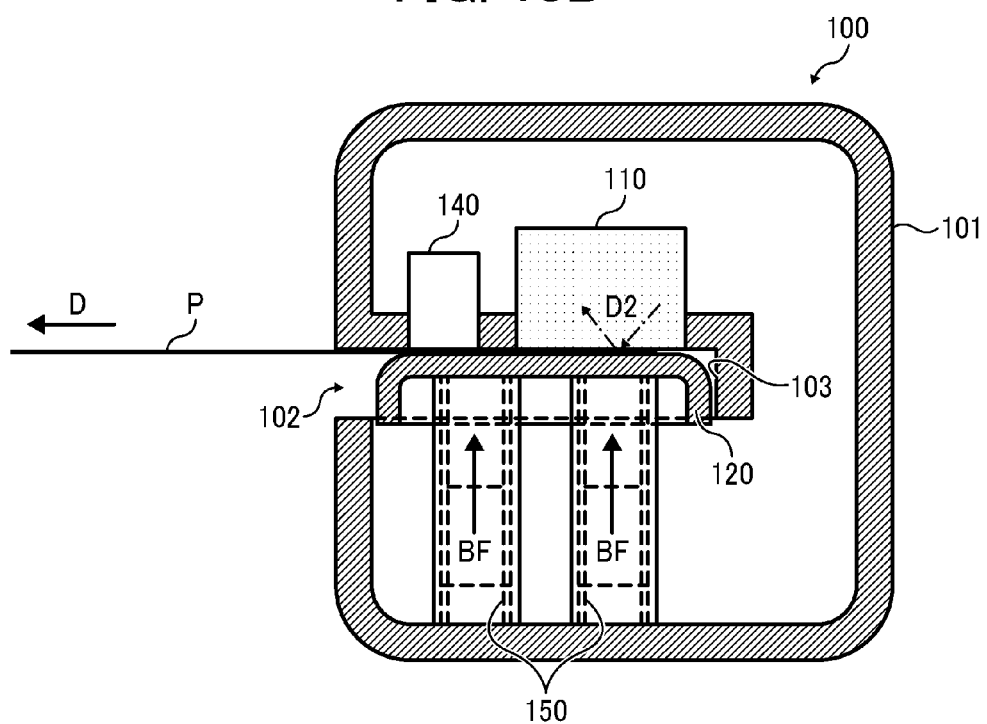
FIG. 13B is a cross sectional view illustrating the sheet discriminator of FIG. 13A when the sheet is pulled out from the opening of the sheet discriminator.

Now, a description is given of a sheet discriminator 100 according to another example of this disclosure, with reference to FIGS. 13A and 13B.

FIGS. 13A and 13B are cross sectional views of the sheet discriminator 100, viewed from a direction indicated by arrow A in FIG. 1. Specifically, FIG. 13A is a cross sectional view illustrating the sheet discriminator 100 when the sheet P is inserted thereto through the opening 102 of the sheet discriminator 100 and FIG. 13B is a cross sectional view illustrating the sheet discriminator 100 when the sheet P is pulled out from the opening 102 of the sheet discriminator 100.

The sheet discriminator 100 according to this example further includes a sheet detecting sensor 140 that detects whether there is the sheet P at a detection position.

In the sheet discriminator 100 according to this example, the sheet information detecting sensor 110 and a sheet detecting sensor 140 are aligned in this order in the sheet inserting direction indicated by arrow C illustrated in FIGS. 13A and 13B.

It is to be noted that the positions of the sheet information detecting sensor 110 and the sheet detecting sensor 140 in the sheet inserting direction can be switched from those illustrated in FIGS. 13A and 13B.

Similar to the sheet information detecting sensor 110, the sheet detecting sensor 140 is connected to the controller 600. Based on detection results obtained by the sheet detecting sensor 140, the controller 600 controls start and stop of light emission of the light source 111 of the sheet information detecting sensor 110 via the light emission processing unit 130 (see FIG. 4).

It is to be noted that the configuration of the sheet discriminator 100 illustrated in FIGS. 13A and 13B is basically identical to the configuration of the sheet discriminator 100 illustrated in FIGS. 3A through 3C. Therefore, detailed descriptions of the other components and functions are omitted here.

In the sheet discriminator 100 according to this example, when the sheet P is inserted into the opening 102 and the sheet detecting sensor 140 detects the sheet P at the detection position, the controller 600 causes the sheet information detecting sensor 110 to start the information detection (e.g., the first information detection D1). At this time, the sheet information detecting sensor 110 detects information of the sheet P for multiple times at the given detection intervals (the sampling periods).

Thereafter, if the sheet detecting sensor 140 detects that there is no sheet at the detection position when the sheet P is pulled out from the opening 102, the controller 600 causes the sheet information detecting sensor 110 to stop the information detection. Then, the controller 600 discriminates the sheet P based on the detected information of the sheet P obtained by the sheet information detecting sensor 110.

Further, the given detection intervals (the sampling periods) of sheet information detected by the sheet information detecting sensor 110 may be optionally set and/or changed by a service representative or a user. By so doing, as the detection intervals of sheet information of the sheet P become shorter (as the sampling periods of sheet information of the sheet P are more accelerated), more detection results can be obtained at the same amount of movement of the sheet P in the opening 102. As a result, more precise discrimination of the sheet P can be performed.

Figure 14:
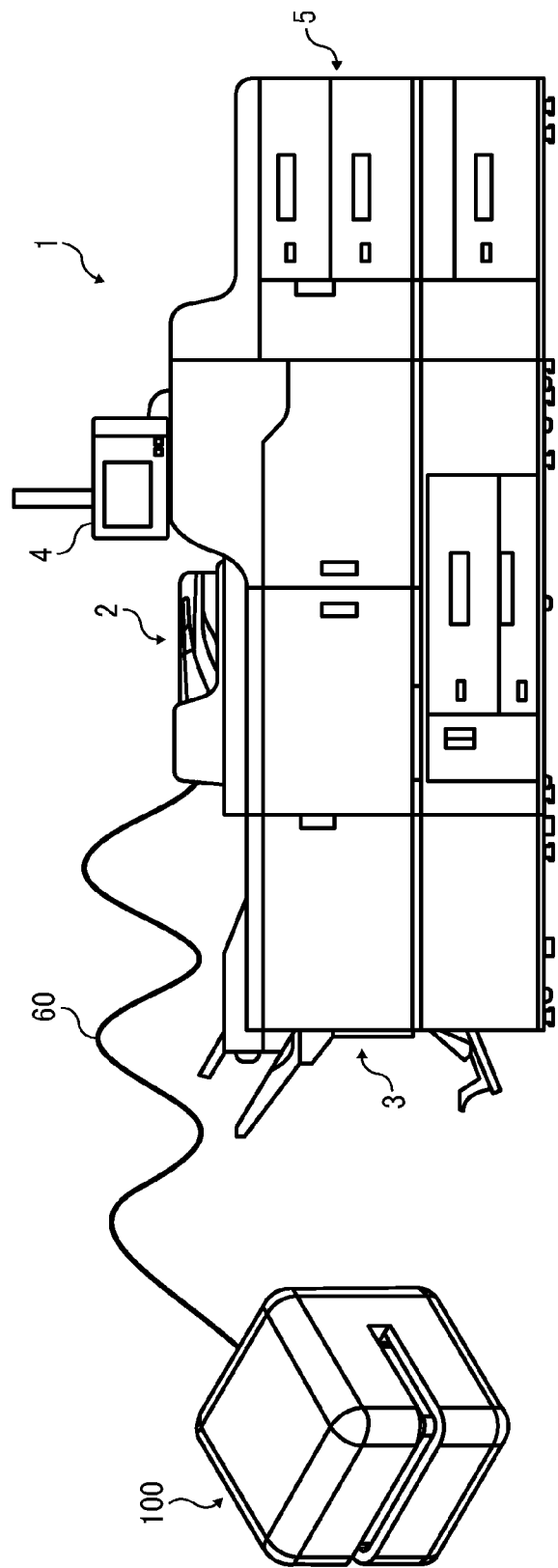
FIG. 14 is a diagram illustrating a configuration of an image forming system according to an example of this disclosure.

Next, a description is given of a configuration of an image forming system 1 according to another example of this disclosure, with reference to FIG. 14.

FIG. 14 is a diagram illustrating a configuration of an image forming system 1 according to an example of this disclosure.

As illustrated in FIG. 14, the image forming system 1 includes an image forming apparatus 2, a sheet finishing apparatus 3 that functions as a sheet finisher, and an optional unit 5 including a sheet tray or sheet trays to accommodate the sheet P therein.

Further, the sheet discriminator 100 is disposed in the image forming system 1 outside the image forming apparatus 2.

The image forming apparatus 2, the sheet finishing apparatus 3, and the optional unit 5 are connected to communicate with each other. In the image forming system 1, after the image forming apparatus 2 has formed an image on the sheet P, the sheet finishing apparatus 3 accepts the sheet P from the image forming apparatus 2 for various post-processing operations to the sheet P.

The post-processing operations include, for example, a corner binding process, a center folding process, and the like. The center folding process includes a center binding process. The sheet finishing apparatus 3 that executes the above-described various post-processing operations includes a sheet ejection mode, a corner binding mode, and a center binding mode.

Figure 15:
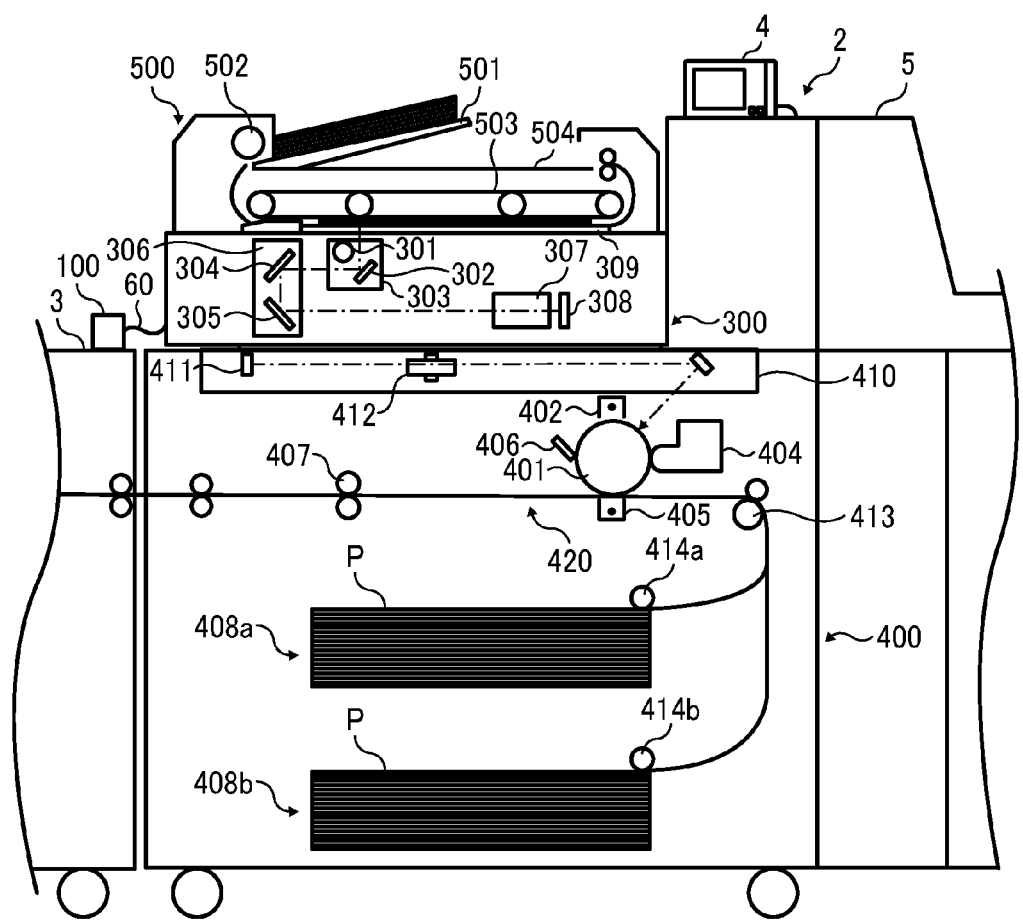
FIG. 15 is a diagram illustrating a configuration of an image forming apparatus included in the image forming system of FIG. 14.

FIG. 15 is a diagram illustrating a configuration of the image forming apparatus 2 included in the image forming system 1 of FIG. 14.

The image forming apparatus 2 may be a copier, a printer, a scanner, a facsimile machine, a plotter, and a multifunction peripheral or a multifunction printer (MFP) having at least one of copying, printing, scanning, facsimile, and plotter functions, or the like. According to the present example, the image forming apparatus 2 is an electrophotographic printer that forms toner images on a sheet or sheets by electrophotography.

More specifically, the image forming apparatus 2 functions as a printer. However, the image forming apparatus 2 can expand its function as a copier by adding a scanner as an optional unit disposed on top of an apparatus body of the image forming apparatus 2. The image forming apparatus 2 can further obtain functions as a facsimile machine by adding an optional facsimile substrate in the apparatus body of the image forming apparatus 2.

Further, this disclosure is also applicable to image forming apparatuses adapted to form images through other schemes, such as known ink jet schemes, known toner projection schemes, or the like as well as to image forming apparatuses adapted to form images through electro-photographic schemes.

The image forming apparatus 2 includes an apparatus body 400, an image reading device 300, and an automatic document feeder (ADF) 500.

The apparatus body 400 encases an image forming part 420 and sheet trays 408a and 408b therein. The sheet trays 408a and 408b are vertically arranged and disposed below the image forming part 420. The sheet trays 408a and 408b have sheet feed rollers 414a and 414b, respectively, and accommodate the sheet P that functions as a recording medium. After the sheet P being fed by a selected one of the sheet feed rollers 414a and 414b, the sheet P accommodated in each of the sheet trays 408a and 408b is conveyed upwardly along a corresponding conveying path before reaching the registration roller pair 413.

The image forming part 420 includes a photoconductor drum 401 that functions as an image bearer, a charger 402, an exposing device 410, a developing device 404, a transfer device 405, and a cleaning device 406.

The charger 402 uniformly charges a surface of the photoconductor drum 401.

The exposing device 410 is a latent image forming device to form an electrostatic latent image on the surface of the photoconductor drum 401 based on image data read by the image reading device 300.

The developing device 404 supplies toner to adhere to the electrostatic latent image formed on the surface of the photoconductor drum 401 and develops the electrostatic latent image into a visible toner image.

The transfer device 405 is an image transfer body to transfer the visible toner image on the photoconductor drum 401 onto the sheet P.

The cleaning device 406 is a cleaner to remove residual toner remaining on the surface of the photoconductor drum 401 after transfer of the toner image onto the sheet P.

The image forming apparatus 2 further includes a fixing device 407 that is disposed downstream from the image forming part 420 in a sheet conveying direction. The fixing device 407 functions as a fuser to fix the toner image to the sheet P.

The exposing device 410 include a laser unit 411 and a polygon mirror 412.

The laser unit 411 emits laser light based on the image data under control of a controller provided to the apparatus body 400.

The polygon mirror 412 scans the laser light emitted by the laser unit 411 in a direction of rotational axis of the photoconductor drum 401 (in a main scanning direction).

The image reading device 300 functions as an image reader to read image data of an original document.

The ADF 500 is disposed above the image reading device 300 and is connected to the image reading device 300. The ADF 500 includes a document table 501, a document feed roller 502, a transfer belt 503, and a document ejecting tray 504.

When original documents are set on the document table 501, upon receipt of a signal to start reading image data of the original documents, the document feed roller 502 of the ADF 500 feeds the original documents placed on the document table 501 one by one. Each original document fed by the document feed roller 502 is guided by the transfer belt 503 to a contact glass 309 and is halted on the contact glass 309 temporarily.

With the original document temporarily halted on the contact glass 309, the image reading device 300 reads the image data of the original document. Thereafter, the transfer belt 503 resumes conveyance of the original document to discharge the original document to the document ejecting tray 504.

Next, a description is given of a series of image reading processes and a series of image forming processes.

Either when the ADF 500 feeds the original document to the contact glass 309 or when a user places the original document on the contact glass 309 manually and inputs a copy start instruction via a control panel 4 mounted on the image forming apparatus 2, a light source 301 mounted on the first moving unit 303 emits light. Along with the light emission, the first moving unit 303 and the second moving unit 306 are moved along a guide rail or guide rails.

As the light source 301 emits the light onto the original document placed on the contact glass 309, the reflection light reflects on the original document. The reflection light is guided to a mirror 302 mounted on the first moving unit 303 and mirrors 304 and 305 mounted on the second moving unit 306, and a lens 307 so as to be received by a CCD 308.

As a result, the CCD 308 reads the image data of the original document and the read image data is converted from analog data to digital data by an analog/digital (A/D) conversion circuit provided to the image forming apparatus 2. The image data is then transmitted from a data output port of the image reading device 300 to the controller of the apparatus body 400.

By contrast, the apparatus body 400 starts driving the photoconductor drum 401. As the photoconductor drum 401 rotates and reaches at a given speed, the charger 402 uniformly charges the surface of the photoconductor drum 401. The exposing device 410 then exposes light to the surface of the photoconductor drum 401 to form an electrostatic latent image based on the image data read by the image reading device 300.

Then, the developing device 404 develops the electrostatic latent image formed on the surface of the photoconductor drum 401 into a visible toner image.

The sheet P is fed from a selected one of the sheet trays 408a and 408b by a corresponding one of the sheet feed rollers 414a and 414b and is temporarily stopped at the registration roller pair 413. Alternatively, the sheet P accommodated in a sheet tray provided to the optional unit 5 is fed from the optional unit 5 to the image forming apparatus 2, and is temporarily stopped at the registration roller pair 413.

In synchronization with timing at which the leading end of the toner image formed on the surface of the photoconductor drum 401 reaches an image transfer part that is located facing the transfer device 405, the registration roller pair 413 resumes the rotation and conveys the sheet P to the image transfer part. When the sheet P passes the image transfer part, the toner image formed on the surface of the photoconductor drum 401 is transferred onto the sheet P due to an action of an electric field in a transfer nip region.

Thereafter, the sheet P having the toner image on the surface thereof is conveyed to the fixing device 407, where the toner image is fixed to the sheet P. Then, the sheet P is ejected to the sheet finishing apparatus 3.

It is to be noted that residual toner remaining on the surface of the photoconductor drum 401 without being transferred onto the sheet P at the image transfer part is removed from the photoconductor drum 401 by the cleaning device 406.

Figure 16:
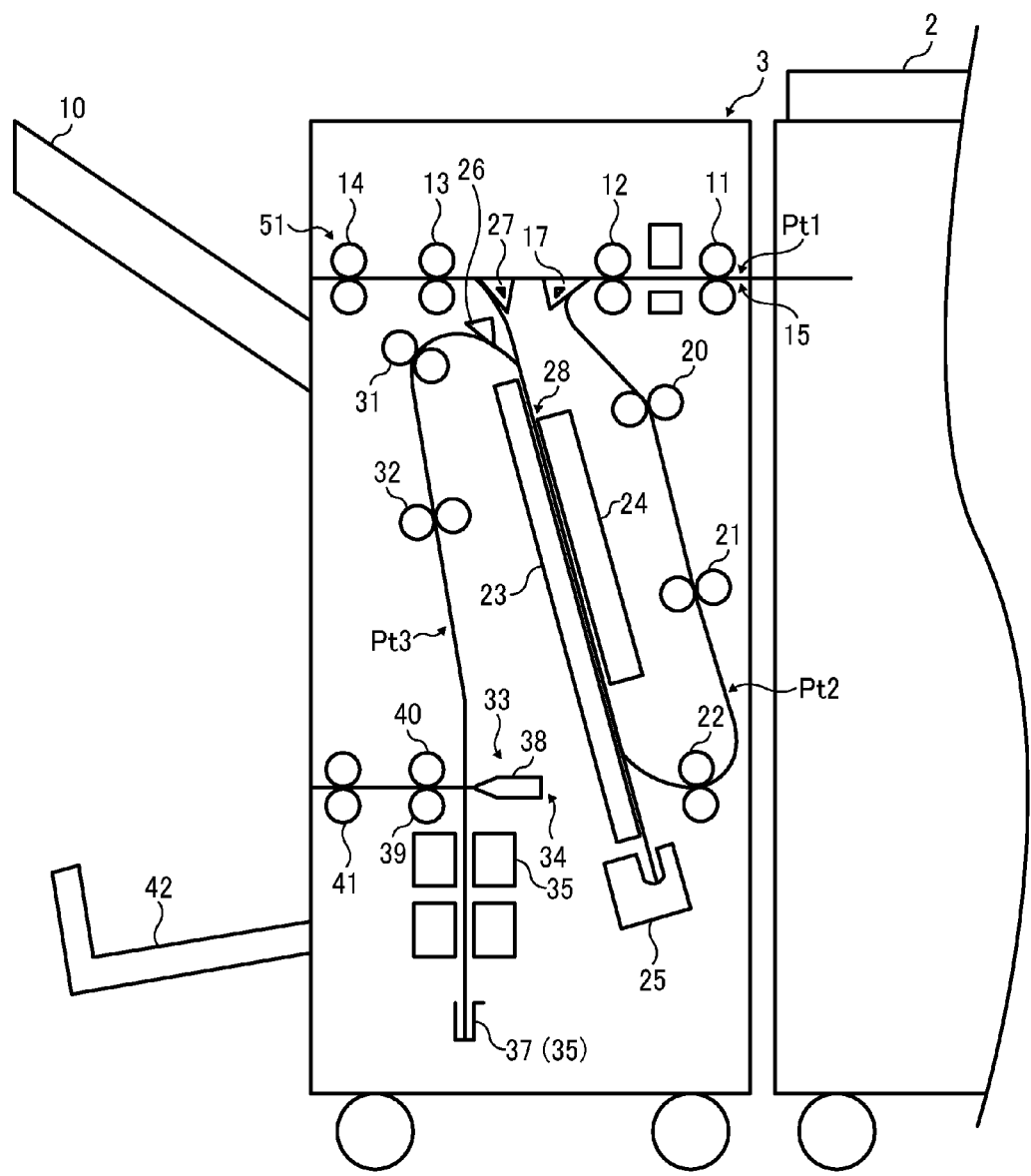
FIG. 16 is a diagram illustrating a configuration of a sheet finisher included in the image forming system of FIG. 14.

A description is given of the sheet finishing apparatus 3 with reference to FIG. 16.

FIG. 16 is a diagram illustrating a configuration of the sheet finishing apparatus 3 included in the image forming system 1 illustrated in FIG. 14.

The sheet finishing apparatus 3 includes a first conveying path Pt1, a second conveying path Pt2, and a third conveying path Pt3.

The first conveying path Pt1 is a path through which the sheet P ejected from the image forming apparatus 2 travels to the first sheet ejecting tray 10.

The second conveying path Pt2 branches from the first conveying path Pt1 to perform a side-stitching operation to a bundle of sheets.

The third conveying path Pt3 is connected to the second conveying path Pt2 to perform a saddle-stitched center-folded sheet bundling operation to the bundle of sheets.

The first conveying path Pt1, the second conveying path Pt2, and the third conveying path Pt3 are defined by guide members, for example.

The first conveying path Pt1 includes an entrance roller 11, a sheet conveying roller 12, a sheet conveying roller 13, and a sheet ejecting roller 14, which are disposed in this order along the first conveying path Pt1 from an upstream side to a downstream side of the sheet conveying direction.

The entrance roller 11, the sheet conveying roller 12, the sheet conveying roller 13, and the sheet ejecting roller 14 are driven by a motor that functions as a driving source to convey the sheet P.

The first conveying path Pt1 further includes an entrance sensor 15 disposed upstream from the entrance roller 11 in the sheet conveying direction. The entrance sensor 15 detects that the sheet P is conveyed into the sheet finishing apparatus 3.

A bifurcating claw 17 is disposed downstream from the sheet conveying roller 12 in the sheet conveying direction. The bifurcating claw 17 rotates to switch the position to selectively guide the sheet P to one of a downstream side of the bifurcating claw 17 in the first conveying path Pt1 in the sheet conveying direction and the second conveying path Pt2. The bifurcating claw 17 is driven by a motor or a solenoid.

In a sheet ejecting mode, the sheet P conveyed from the image forming apparatus 2 to the first conveying path Pt1 is conveyed by the entrance roller 11, the sheet conveying roller 12, the sheet conveying roller 13, and the sheet ejecting roller 14, and is ejected to the first sheet ejecting tray 10.

By contrast, in a side stitching mode and a center folding mode, the sheet P entered into the first conveying path Pt1 is conveyed by the entrance roller 11 and the sheet conveying roller 12, has a course of direction changed by the bifurcating claw 17, and is conveyed to the second conveying path Pt2.

The second conveying path Pt2 includes a sheet conveying roller 20, a sheet conveying rollers 21, 22, and 23, a first sheet aligning part 24, and a side-stitching unit (a first stitching unit) 25.

The sheet conveying rollers 20, 21, and 22 are driven by a motor. The first sheet aligning part 24 is driven by the motor.

Bifurcating claws 26 and 27 are disposed at a downstream side of the sheet tray 23 in the sheet conveying direction. The bifurcating claws 26 and 27 rotate to switch respective positions, so that the sheet P is selectively guided to one of the downstream side of the bifurcating claw 17 in the first conveying path Pt1 and the third conveying path Pt3. The bifurcating claws 26 and 27 are driven by a motor or a solenoid, for example.

In the side stitching mode, multiple sheets P are sequentially loaded on the selected one of the sheet trays 23. By so doing, the sheets including the multiple sheets P loaded thereon is made to a sheet bundle. At this time, the trailing end of the bundle of sheets contacts a first movable reference fence that is disposed to the sheet tray 23 to align a position in the sheet conveying direction and a width position by the first sheet aligning part 24.

The sheet tray 23, the first sheet aligning part 24, and the first movable reference fence form a first bundling part 28 that functions as a bundling part to make multiple sheets into a stacked sheet bundle. The first bundling part 28 further includes a motor to drive the first sheet aligning part 24 and a motor to drive the first movable reference fence.

The side-stitched sheet bundle is conveyed by the first movable reference fence to the first conveying path Pt1. Then, the sheet bundle is further conveyed by the sheet conveying roller 13 and the sheet ejecting roller 14 to be ejected to the first sheet ejecting tray 10.

Here, the sheet ejecting roller 14 functions as a sheet ejecting member to eject the sheet bundle that is bundled by the side stitching unit 25. By contrast, in the center folding mode, the sheet P conveyed to the second conveying path Pt2 is conveyed to the third conveying path Pt3 by the sheet conveying rollers 20, 21, and 22, and the first movable reference fence.

The third conveying path Pt3 includes sheet conveying rollers 31 and 32, and a binding and folding part 33.

A motor drives the sheet conveying rollers 31 and 32 to convey the sheet P. The binding and folding part 33 includes a center folding part 34, a saddle-stitching part (a second stitching unit) 35, and a second bundling part 36.

The sheet P conveyed to the third conveying path Pt3 is conveyed by the sheet conveying rollers 31 and 32 one by one to the second bundling part 36. As a result, a sheet bundle of layered multiple sheets P is made. Specifically, the second bundling part 36 makes a stacked sheet bundle with multiple sheets conveyed by a sheet conveying part 51 that includes the entrance roller 11 and the sheet conveying rollers 12, 20, 21, 22, 31, and 32.

At this time, the leading end of the sheets P of the sheet bundle contacts a second movable reference fence 37 to be aligned in the sheet conveying direction and contacts a second sheet aligning part to be aligned in a sheet width direction.

The saddle-stitching part 35 stitches the sheet bundle at or in the vicinity of the center of the sheet bundle in the sheet conveying direction. The saddle-stitched sheet bundle is returned to a center folding position by the second movable reference fence 37. The second movable reference fence 37 is driven by a motor.

The center folding part 34 folds the sheet bundle at the center thereof in the sheet conveying direction. In the center folding part 34, a folding blade 38 is disposed facing the center of the sheet bundle in the sheet conveying direction. The folding blade 38 that is driven by a motor moves from right to left of FIG. 16 to fold the center of the sheet bundle in the sheet conveying direction to insert the sheet bundle between a lower pressure roller 39 and an upper pressure roller 40.

The folded sheet bundle is pressed vertically in an upward direction by the lower pressure roller 39 and a downward direction by the upper pressure roller 40. The lower pressure roller 39 and the upper pressure roller 40 are driven by a motor.

The above-described center-folded sheet bundle is ejected by the lower pressure roller 39, the upper pressure roller 40, and a sheet ejecting roller 41 to a second sheet ejecting tray 42.

Figure 17:
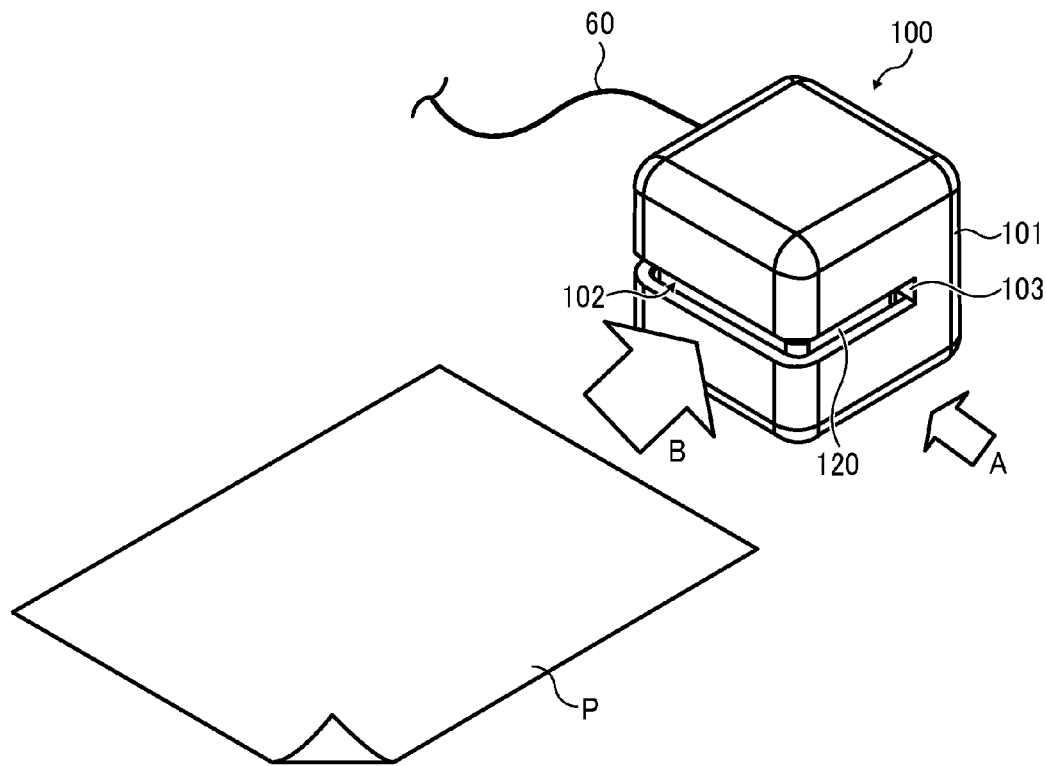
FIG. 17 is a diagram illustrating another configuration of a sheet discriminator included in the image forming system of FIG. 14.

A description is given of another example of the sheet discriminator 100 according to this example, with reference to FIG. 17.

FIG. 17 is a diagram illustrating another configuration of the sheet discriminator 100 included in the image forming system 1 of FIG. 14.

It is to be noted that the basic configuration of the sheet discriminator 100 illustrated in FIG. 17 is basically identical to the sheet discriminator 100 illustrated in FIGS. 1 and 2A, and therefore a detailed description of the configuration of the sheet discriminator 100 according to this example is omitted.

The sheet discriminator 100 according to this example is connected with the image forming apparatus 2 by a communication cable 60 that functions as a communicator such as a universal serial bus (USB) cable and a local area network (LAN) cable. According to this configuration, the sheet discriminator 100 and the image forming apparatus 2 can communicate with each other.

By connecting the image forming apparatus 2 and the sheet discriminator 100 via the communication cable 60, the results of sheet information detected by the sheet information detecting sensor 110 and the results of discrimination of the sheet P can be shared therebetween.

As a result, when a new image forming operation is performed, the time and effort of a user to manually input the image forming conditions corresponding to the sheet P used for the image forming operation can be saved. At the same time, human error such as incorrect setting can be avoided.

Figure 18:
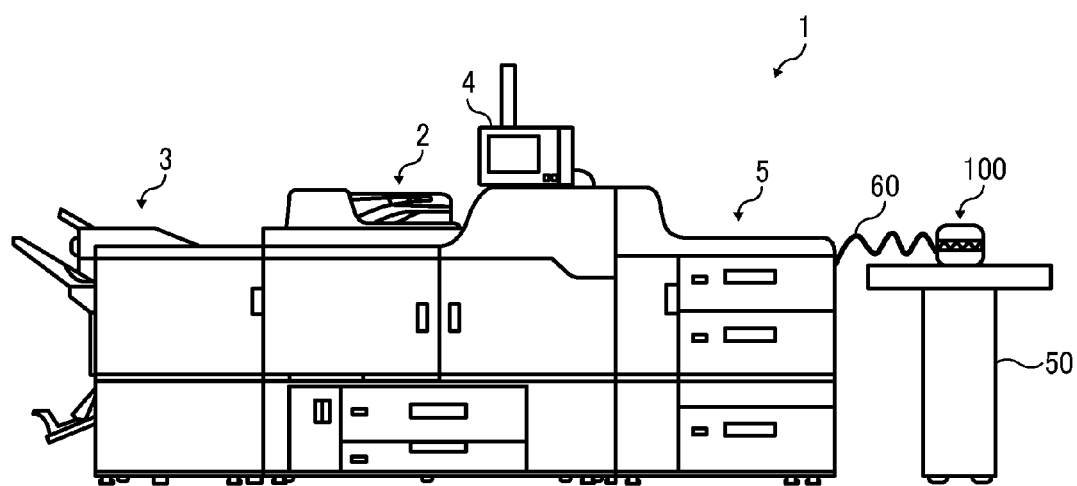
FIG. 18 is a diagram illustrating a configuration of an image forming system with a sheet discriminator installed on an installation table, according to another example of this disclosure.

A description is given of the image forming system 1 according to another example of this disclosure, with reference to FIG. 18.

FIG. 18 is a diagram illustrating a configuration of the image forming system 1 with the sheet discriminator 100 mounted on an installation table 50.

The installation table 50 is located in the vicinity of the image forming apparatus 2 and is dedicated to the installation table 50.

As described above, by disposing the sheet discriminator 100 on the installation table 50 located in the vicinity of the image forming apparatus 2, a user can obtain information of the sheet P to be used for a subsequent printing operation with the sheet discriminator 100 even while a different user is operating the image forming apparatus 2. As a result, occurrence of downtime caused by setting of type of the sheet P can be reduced.

Figure 19:
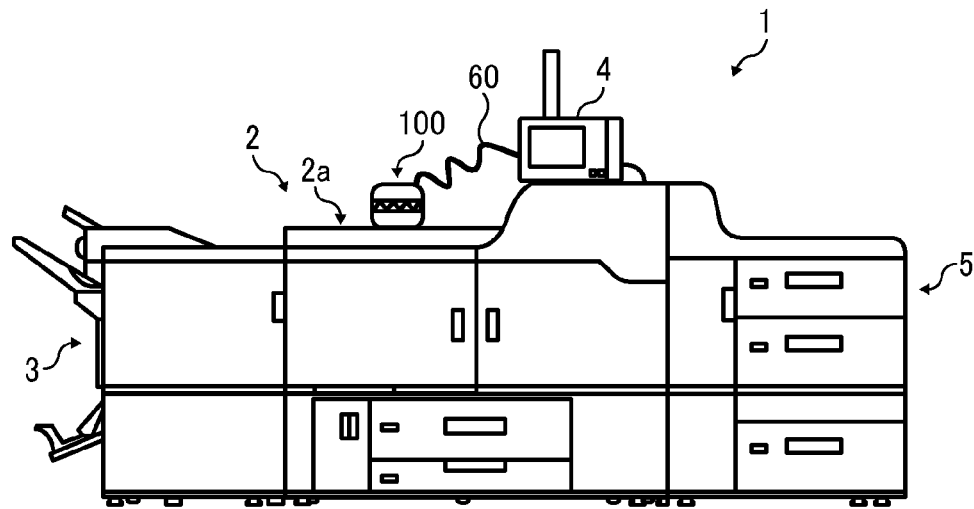
FIG. 19 is a diagram illustrating a configuration of the image forming system with the sheet discriminator installed on an image forming apparatus, according to another example of this disclosure.

A description is given of the image forming system 1 according to yet another example of this disclosure, with reference to FIG. 19.

FIG. 19 is a diagram illustrating a configuration of the image forming system 1 with the sheet discriminator 100 installed on the image forming apparatus 2.

As illustrated in FIG. 19, the ADF 500 is removed from the image forming apparatus 2 and is replaced by the sheet discriminator 100. Specifically, the sheet discriminator 100 is placed on an apparatus top face 2a of the image forming apparatus 2, on which the ADF 500 was placed.

As described above, by disposing the sheet discriminator 100 on the apparatus top face 2a of the image forming apparatus 2, a sheet discriminating function can be additionally implemented and an increase in an installation area of the whole image forming system for installing the sheet discriminator 100 can be avoided.

Figure 20:
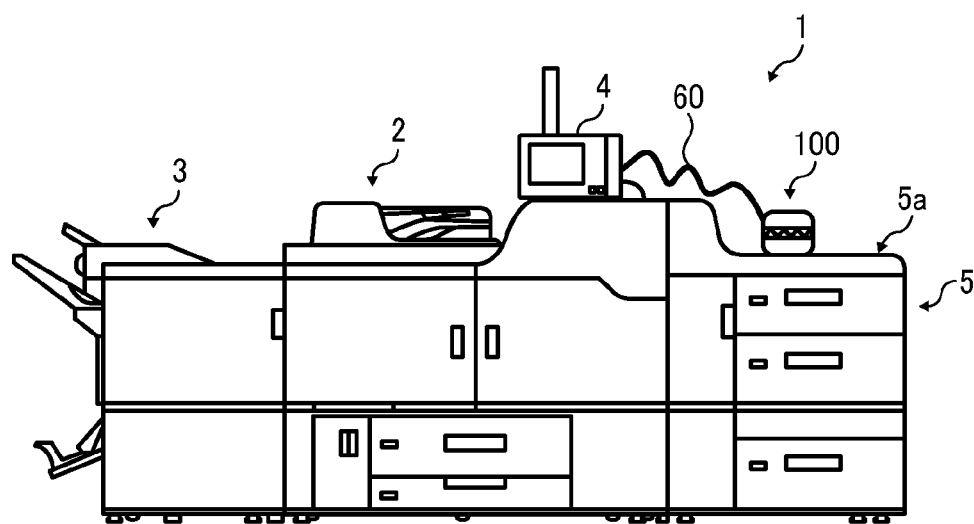
FIG. 20 is a diagram illustrating, a configuration of the image forming system with the sheet discriminator installed on a top surface of an optional unit, according to another example of this disclosure.

A description is given of the image forming system 1 according to yet another example of this disclosure, with reference to FIG. 20.

FIG. 20 is a diagram illustrating a configuration of the image forming system 1 with the sheet discriminator 100 installed on a top face of the optional unit 5.

As illustrated in FIG. 20, the sheet discriminator 100 is placed on a unit top face 5a of the optional unit 5, to which an additional sheet feeding unit is provided.

As described above, by disposing the sheet discriminator 100 on the unit top face 5a of the optional unit 5, even when the image forming apparatus 2 cannot spare an installation space for the sheet discriminator 100, a sheet discriminating function can be additionally implemented and an increase in an installation area of the whole image forming system for installing the sheet discriminator 100 can be avoided.

Further, in the examples illustrated in FIGS. 19 and 20, a user can conduct sheet discrimination with the sheet discriminator 100 at a position relatively close to the control panel 4 of the image forming apparatus 2.

As a result, the communication cable 60 transmits the results of discrimination of the sheet P from the sheet discriminator 100 to the image forming apparatus 2, so that a user can easily check the results of discrimination of the sheet P displayed on a display of the control panel 4. Accordingly, nuisance of the user such as moving and setting to check the results of discrimination of the sheet P can be eliminated, and the sheet information can be checked and an appropriate sheet for the current image forming operation can be determined smoothly.

A description is given of a control of sheet discrimination with reference to FIGS. 17, 21A, 21B, and 22.

FIGS. 21A and 21B are cross sectional views of the sheet discriminator 100, viewed from a direction indicated by arrow A in FIG. 17. Specifically, FIG. 21A is a cross sectional view illustrating the sheet discriminator 100 when the sheet P is inserted thereto through the opening 102 of the sheet discriminator 100 and FIG. 21B is a cross sectional view illustrating the sheet discriminator 100 when the sheet P is pulled out from the opening 102 of the sheet discriminator 100.

Figure 22:
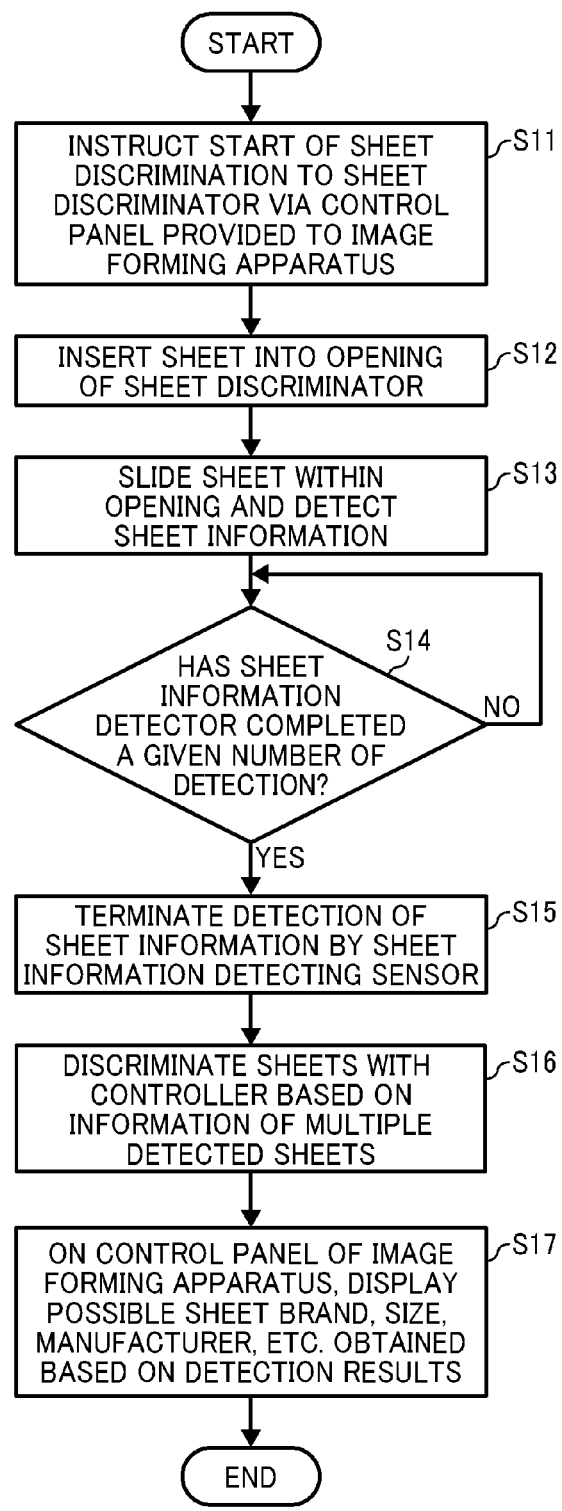
FIG. 22 is a flowchart illustrating an example of control of sheet discrimination performed by the sheet discriminator of FIGS. 21A and 21B.

FIG. 22 is a flowchart illustrating an example of control of sheet discrimination performed by the sheet discriminator 100 of FIGS. 21A and 21B.

The control of sheet discrimination is described with reference to FIGS. 21A, 21B, and 22.

It is to be noted that the sheet information detecting sensor 110 detects information of the sheet P for multiple times at the given detection intervals (the sampling periods).

The sheet discriminator 100 that is connected with the image forming apparatus 2 via the communication cable 60 receives instructions to start the sheet discrimination of the sheet P via the control panel 4 that is mounted on the image forming apparatus 2, as described in step S11 in the flowchart of FIG. 22. After the operation of step S11 in FIG. 22 is completed, the light emission processing unit 130 of the sheet discriminator 100 causes the sheet information detecting sensor 110 to start detecting information of the sheet P.

Then, as illustrated in FIG. 21A, the sheet P is inserted toward the end face 103 of the opening 102 of the sheet discriminator 100 in the direction C, as described in step S12 in the flowchart of FIG. 22.

At this time, it is preferable that an operator grips both left and right ends of the sheet P by hands with respect to the direction C and inserts the sheet P while checking that the sheet P has no deformation such as wrinkle or crease on the sheet P. It is to be noted that sheet insertion to the opening 102 is not limited to the above-described way but is applicable with any way of sheet insertion as long as the sheet P can be inserted into the opening 102 of the sheet discriminator 100 horizontally.

When the sheet P passes a position facing the sheet information detecting sensor 110, the sheet information detecting sensor 110 performs the first information detection D1 in FIG. 21A with respect to the sheet P that is inserted toward the end face 103 of the opening 102.

After the sheet P has reached the end face 103 of the opening 102, the sheet P is removed. When pulling out the sheet P from the opening 102, the sheet P moves in a direction indicated by arrow D in FIG. 21B. At this time, the sheet information detecting sensor 110 performs a second information detection D2 in FIG. 21B. Accordingly, the sheet information detecting sensor 110 detects the sheet P at different points on the sheet P in the first information detection and the second information detection.

As described above, the sheet discriminator 100 according to this example slides the sheet P in the opening 102 of the sheet discriminator 100 for multiple detections of the information of the sheet P, as described in step S13 in the flowchart of FIG. 22.

After the sheet information detecting sensor 110 has detected the sheet P for given times (e.g., two times in this example), which is YES in step S14 in FIG. 22, the controller 600 causes the sheet information detecting sensor 110 to stop the detection of information of the sheet P, as described in step S15 in FIG. 22. Then, the controller 600 discriminates the sheet P based on the sheet information obtained from the multiple points on the sheet P, as described in step S16 in the flowchart of FIG. 22.

When the sheet information detecting sensor 110 has not detected the sheet P for the given times, which is NO in step S14 in the flowchart of FIG. 22, the procedure is repeated until the condition of step S14 is satisfied.

As described above, the controller 600 discriminates the sheet P based on the sheet information obtained from the multiple points on the sheet P. This operation encourages averaging discrimination results and obtaining the median value of the discrimination results, and therefore measurement errors such as noise can be reduced or prevented and more precise discrimination of the sheet P can be achieved.

Further, based on detection results regarding the sheet P obtained by the sheet discriminator 100, possible sheet brands including sizes, manufacturers, etc. of the sheet P that is inserted into the sheet discriminator 100 through the opening 102 are displayed on a display of the control panel 4, as described in step S17 in the flowchart of FIG. 22. Then, the controller 600 completes the control of sheet discrimination using the sheet discriminator 100 illustrated in FIGS. 21A and 21B, and sets the image forming conditions according to a correct type of the sheet P out of the listed sheet brands including sizes, and so forth displayed on the control panel 4 to perform image formation.

Further, given detection intervals (sampling periods) of sheet information detected by the sheet information detecting sensor 110 may be optionally set and/or changed by a service representative or a user. By so doing, as the detection intervals of sheet information of the sheet P become shorter (as the sampling periods of sheet information of the sheet P are more accelerated), more detection results can be obtained at the same amount of movement of the sheet P in the opening 102. As a result, more precise discrimination of the sheet P can be performed.

It is to be noted that the image forming apparatus 2 included in the image forming system 1 according to this example can be any one of a digital copier, a printer, an offset printer, and other image forming apparatuses.

It is also to be noted that the sheet discriminator 100 mounted on the image forming apparatus 2 can be any one of the sheet discriminators 100 according to the above-described examples of this disclosure.

Next, a description is given of a configuration of an image forming system 1 according to another example of this disclosure.

It is to be noted that the basic configuration of the image forming system 1 according to this example is basically identical to the above-described image forming system 1 illustrated in FIG. 14, and therefore a detailed description of the configuration of the image forming system 1 according to this example is omitted.

Figure 23:
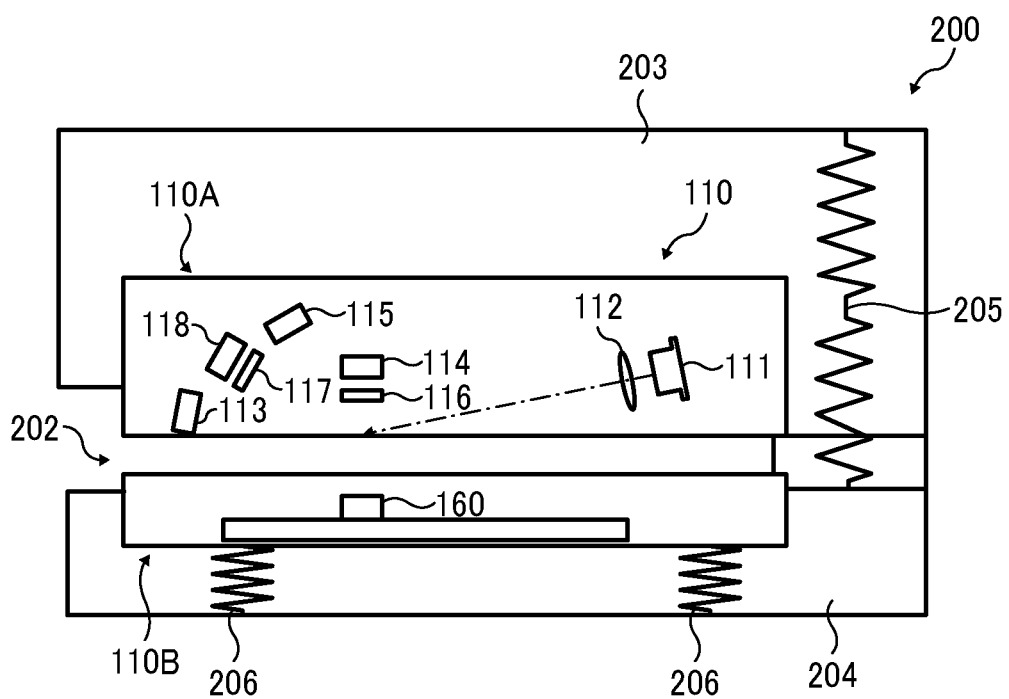
FIG. 23 is a diagram illustrating a sheet discriminator according to another example of this disclosure.

A description is given of another example of the sheet discriminator 200 according to this example, with reference to FIG. 23.

FIG. 23 is a diagram illustrating a sheet discriminator 200 according to another example of this disclosure.

As can be seen from FIG. 23, the configuration of the sheet discriminator 200 according to this example is different from the configuration of the sheet discriminator 100 illustrated in FIGS. 21A and 21B.

The sheet discriminator 200 according to this example is connected with the image forming apparatus 2 included in the image forming system 1 illustrated in FIG. 14 by the communication cable 60. According to this configuration, the sheet discriminator 200 and the image forming apparatus 2 can communicate with each other.

The sheet discriminator 200 includes the sheet information detecting sensor 110 to discriminate types of the sheets P.

The sheet information detecting sensor 110 includes an upper sensor unit 110A and a lower sensor unit 110B. The upper sensor unit 110A includes the light source 111, the collimator lens 112, the receivers 113, 114, 115, and 118 to receive respective light beams diffused on the sheet P, and the polarizing filters 116 and 117. The lower sensor unit 110B includes the receiver 160 to receive a light beam that is transmitted through the sheet P out of the light beams emitted from the light source 111 and irradiated to the sheet P.

It is to be noted that the sheet information detecting sensor 110 included in the sheet discriminator 200 has the same configuration as the sheet information detecting sensor 110 included in the sheet discriminator 100 illustrated in FIGS. 4, 7, 9, and 11, and therefore a detailed description of the configuration of the sheet information detecting sensor 110 according to this example is omitted.

The sheet discriminator 200 further includes an insertion port 202, a sensor unit support 203, a sensor unit support 204, an elastic member 205, and elastic members 206. The insertion port 202 functions as an opening. Each of the elastic members 205 and 206 functions as a biasing member such as a spring.

The upper sensor unit 110A and the lower sensor unit 110B are movably supported with respect to the sensor unit support 203 and the sensor unit support 204, respectively.

It is to be noted that the upper sensor unit 110A, the lower sensor unit 110B, the elastic members 205 and 206 form an adjuster to cause the sheet information detecting sensor 110 to approach and separate with respect to the sheet P.

In a normal state in which no pressure is applied from an outside of the sheet discriminator 200, the upper sensor unit 110A and the lower sensor unit 110B are biased in a direction to separate the upper sensor unit 110A and the lower sensor unit 110B from each other. Therefore, the insertion port 202 is provided between the upper sensor unit 110A and the lower sensor unit 110B and between the sensor unit support 203 and the sensor unit support 204.

The elastic members 206 is disposed between the sensor unit support 204 and the lower sensor unit 110B to connect the sensor unit support 204 and the lower sensor unit 110B each other. The lower sensor unit 110B is vertically movable to the sensor unit support 204 via the elastic members 206.

Figure 24:
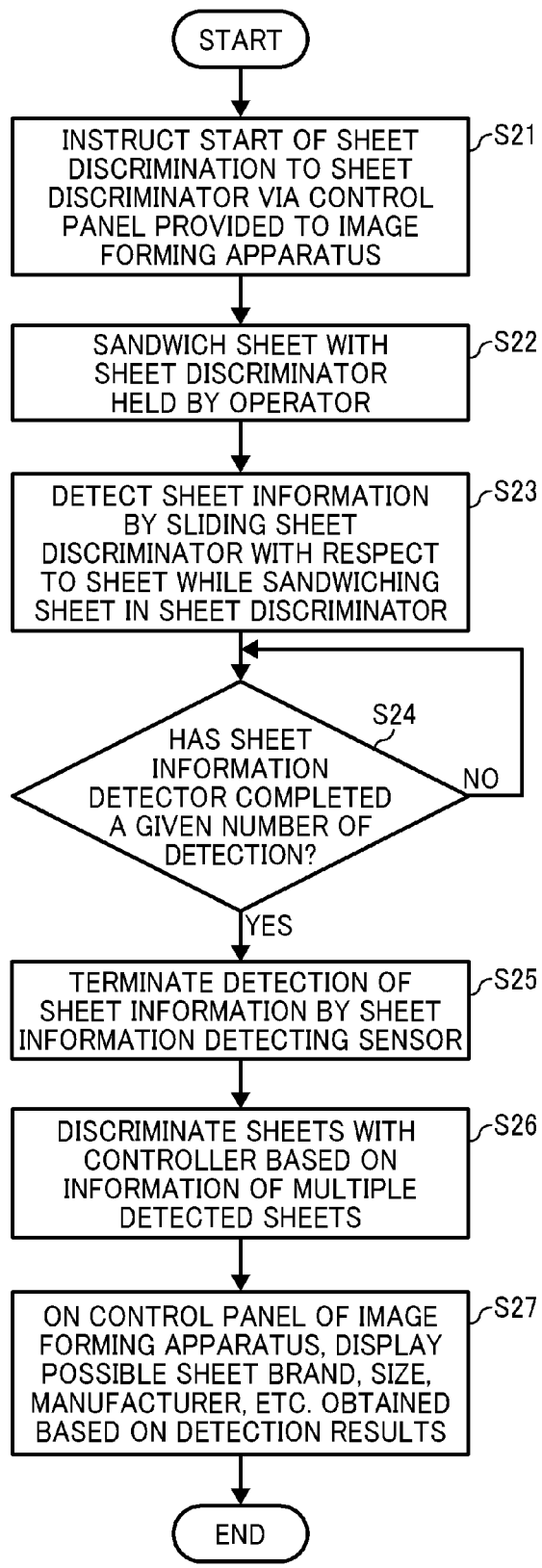
FIG. 24 is a flowchart illustrating an example of control of sheet discrimination performed by the sheet discriminator of FIG. 23.
Figure 25:
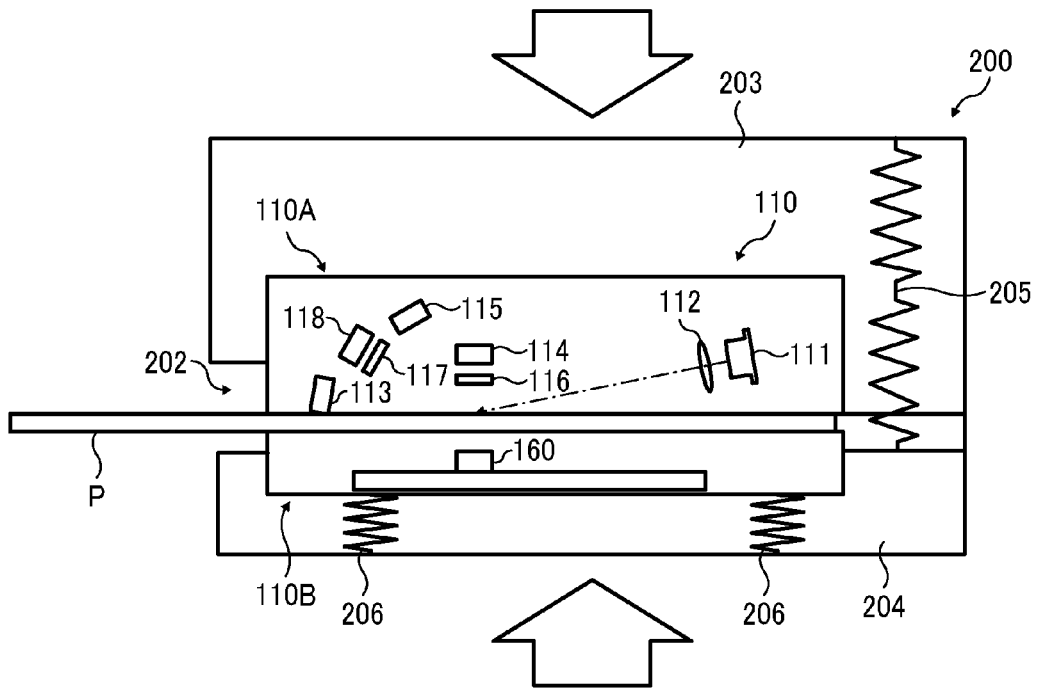
FIG. 25 is a cross sectional view illustrating the sheet discriminator supported by a user with pressure applied from top and bottom in a vertical direction.
Figure 26:
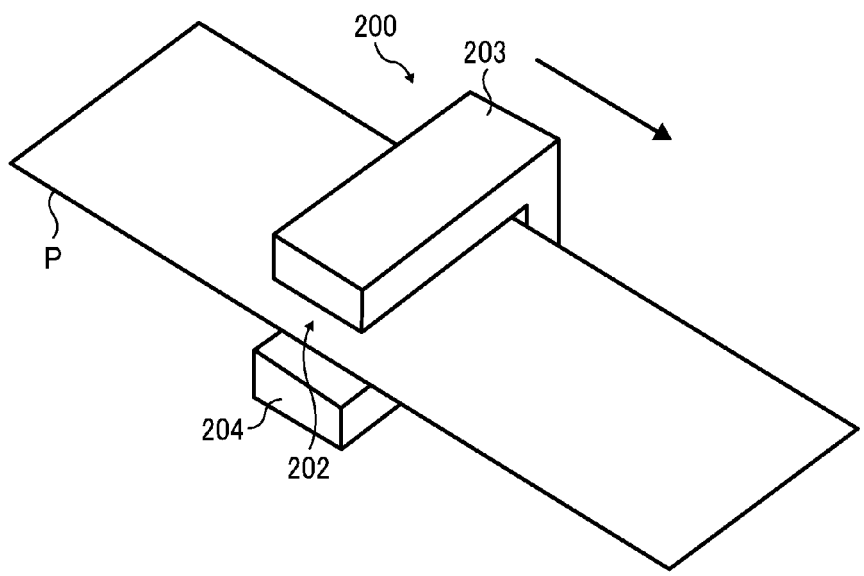
FIG. 26 is a perspective view illustrating the sheet discriminator sliding while sandwiching the sheet.

Next, a description is given of a control of sheet discrimination with reference to FIGS. 24, 25, and 26.

FIG. 24 is a flowchart illustrating an example of control of sheet discrimination performed by the sheet discriminator 200 of FIG. 23. FIG. 25 is a cross sectional view illustrating the sheet discriminator 200 supported by a user with pressure applied from top and bottom in a vertical direction. FIG. 26 is a perspective view illustrating the sheet discriminator 200 sliding while sandwiching the sheet P.

It is to be noted that the sheet information detecting sensor 110 of the sheet discriminator 200 detects information of the sheet P for multiple times at the given detection intervals (the sampling periods).

The sheet discriminator 200 that is connected with the image forming apparatus 2 via the communication cable 60 receives instructions to start the sheet discrimination of the sheet P via the control panel 4 that is mounted on the image forming apparatus 2, as described in step S21 in the flowchart of FIG. 24. After the operation of step S21 in FIG. 24 is completed, the light emission processing unit 130 of the sheet discriminator 100 causes the sheet information detecting sensor 110 to start detecting information of the sheet P.

At this time, it is preferable that an operator holds the sheet discriminator 200 by one hand and the sheet P by the other hand. Then, the operator inserts the sheet P into the insertion port 202 while checking that the sheet P has no deformation such as wrinkle or crease on the sheet P, the operator inserts the sheet P.

Thereafter, for example, the operator places the sheet P on a top face of the lower sensor unit 110B, and then grips the sheet discriminator 200. By so doing, as illustrated in FIG. 25, the pressure is applied from outside to the sensor unit supports 203 and 204 in a vertical direction to press the sheet P from both vertical sides. Specifically, a downward pressure force is applied from outside to the sensor unit support 203 and an upward pressure force is applied from outside to the sensor unit support 204. Accordingly, the pressure (i.e., the downward pressure force and the upward pressure force) causes the sensor unit supports 203 and 204 toward a direction to approach each other, so that the height of the insertion port 202 is reduced.

As a result, the upper sensor unit 110A and the lower sensor unit 110B of the sheet discriminator 200 sandwich the sheet P, as described in step S22 in the flowchart of FIG. 24.

At this time, when the user grips the sheet discriminator 200 with a relatively large force, the elastic members 206 shrink to moving the lower sensor unit 110B downwardly. Accordingly, by lowering the lower sensor unit 110B, the sheet P can be held with a constant force without damaging the sheet P.

Then, the operator slides the sheet discriminator 200 on the sheet P with the sheet P being held therebetween, as illustrated in FIG. 26. Further, while the sheet discriminator 200 is being slid on the sheet P with the sheet P being held therebetween, the sheet discriminator 200 according to this example causes the sheet information detecting sensor 110 to perform multiple detections of the information of the sheet P, as described in step S23 in the flowchart of FIG. 24. By so doing, information of the sheet P can be detected at multiple points on the surface of the sheet P, as illustrated in step S23 in the flowchart of FIG. 24.

After the sheet information detecting sensor 110 has detected the sheet P for given times, which is YES in step S24 in the flowchart of FIG. 24, the controller 600 causes the sheet information detecting sensor 110 to stop the detection of information of the sheet P, as described in step S25 in FIG. 24. Then, the controller 600 discriminates the sheet P based on the sheet information obtained from the multiple points on the sheet P, as described in step S26 in the flowchart of FIG. 24.

When the sheet information detecting sensor 110 has not detected the sheet P for the given times, which is NO in step S24 in the flowchart of FIG. 24, the procedure is repeated until the condition of step S24 is satisfied.

As described above, the controller 600 discriminates the sheet P based on the sheet information obtained from the multiple points on the sheet P. This operation encourages averaging discrimination results and obtaining the median value of the discrimination results, and therefore measurement errors such as noise can be reduced or prevented and more precise discrimination of the sheet P can be achieved.

Further, based on detection results regarding the sheet P obtained by the sheet discriminator 200, possible sheet brands including sizes, manufacturers, etc. of the sheet P are displayed on a display of the control panel 4 of the image forming apparatus 2, as described in step S27 in the flowchart of FIG. 24. Then, the controller 600 completes the control of sheet discrimination using the sheet discriminator 200 illustrated in FIG. 23, and sets the image forming conditions according to a correct type of the sheet P out of the listed sheet brands including sizes, and so forth displayed on the control panel 4 of the image forming apparatus 2 to perform image formation.

It is to be noted that the controller 600 may discriminate the thickness, surface properties, and brand of the sheet P based on the detection results obtained by the sheet information detecting sensor 110.

The sheet information detecting sensor 110 of the sheet discriminator 200 detects information of the sheet P with the sheet P being inserted in the insertion port 202 of the sheet discriminator 200 while the operator checks that there is no deformation such as curls on the sheet P. By so doing, the sheet information detecting sensor 110 does not detect deformed portions on the sheet P and detects correct sheet information of the sheet P, and therefore performance of precise discrimination of sheet types is prevented from being degraded.

Further, given detection intervals (sampling periods) of sheet information detected by the sheet information detecting sensor 110 of the sheet discriminator 200 may be optionally set and/or changed by a service representative or a user. By so doing, as the detection intervals of sheet information of the sheet P become shorter (as the sampling periods of sheet information of the sheet P are more accelerated), more detection results can be obtained at the same amount of movement of the sheet discriminator 200 with respect to the sheet P. As a result, more precise discrimination of the sheet P can be performed.

Figure 27:
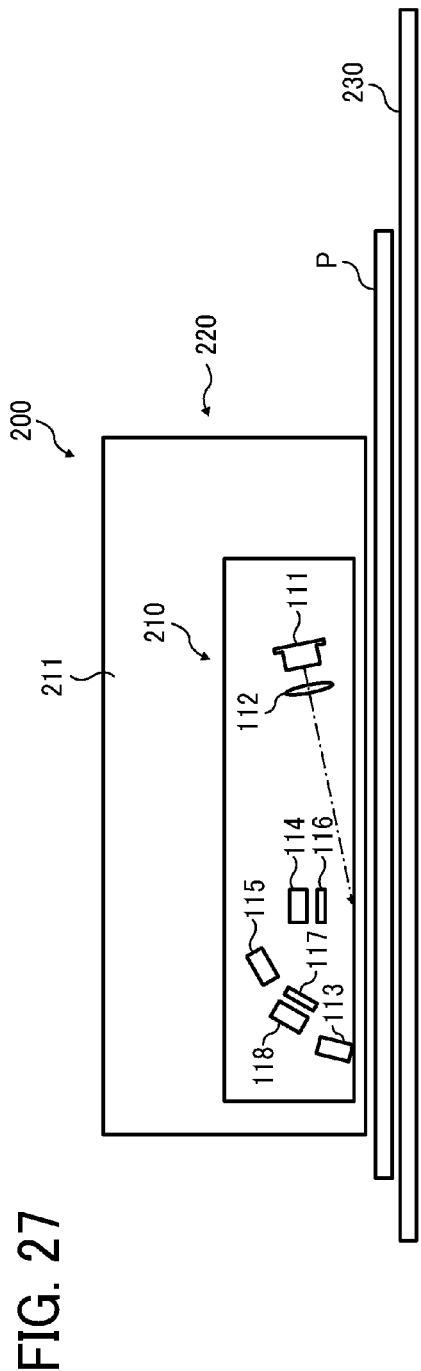
FIG. 27 is a diagram illustrating another configuration of the sheet discriminator.
Figure 28:
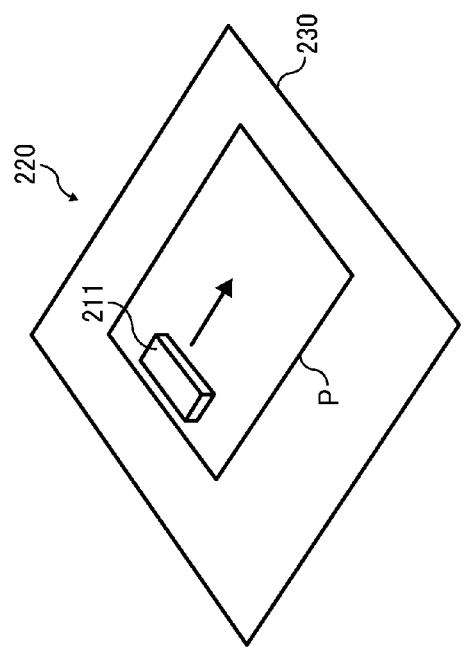
FIG. 28 is a diagram illustrating a sensor holding unit sliding on the sheet.

Next, a description is given of a sheet discriminator 220 according to another example of this disclosure, with reference to FIGS. 27 and 28.

FIG. 27 is a diagram illustrating a configuration of a sheet discriminator 220. FIG. 28 is a diagram illustrating a sensor unit support 211 included in the sheet discriminator 220 to slide on the sheet P.

The sheet discriminator 220 according to this example includes a sheet information detecting sensor 210, a sensor unit support 211 that supports the sheet information detecting sensor 210, and a sheet loading table 230 on which the sheet P is placed.

The sheet information detecting sensor 210 includes an optical sensor having the substantially same configuration as the upper sensor unit 110A of the sheet discriminator 200 as illustrated in FIG. 23.

The sheet discriminator 220 according to this example discriminates the sheet P by not detecting components of transmission light of the sheet P but by detecting components of reflection light of the sheet P.

Next, a description is given of a control of sheet discrimination performed by the sheet discriminator 220.

First, the sheet P that is a detection target is placed on the sheet loading table 230. With this state, the sensor unit support 211 supporting the sheet information detecting sensor 210 is placed on the sheet P.

Then, the operator slides the sheet discriminator 220 on the surface of the sheet P with the sensor unit support 211 placed on the sheet P, as illustrated in FIG. 28. Further, along with this move of the sheet P, the sheet information detecting sensor 210 of the sheet discriminator 220 detects information of the sheet P for multiple times at the given detection intervals (the sampling periods). By so doing, information of the sheet P can be detected at multiple points on the surface of the sheet P.

As described above, the controller 600 discriminates the sheet P based on the sheet information obtained from the multiple points on the sheet P. This operation encourages averaging discrimination results and obtaining the median value of the discrimination results, and therefore measurement errors such as noise can be reduced or prevented and more precise discrimination of the sheet P can be achieved.

It is to be noted that the controller 600 may discriminate the thickness, surface properties, and brand of the sheet P based on the detection results obtained by the sheet information detecting sensor 210.

Further, the sheet discriminator 220 holds (sandwiches) the sheet P between the sensor unit support 211 and the sheet loading table 230. Therefore, a reduction in size of a sheet discriminator and/or an image forming apparatus and a stable operation thereof can be achieved without providing a sheet holding mechanism including an elastic member such as a spring. In other words, the sheet discriminator 220 detects information of the sheet P by fixing the sheet P and moving the sheet discriminator 220, specifically, the sensor unit support 211 on the sheet P. Therefore, nonuniformity of detection performed by a user can be reduced or prevented. As a result, stable outputs of detection results of the sheet P can be achieved.

Further, information of the sheet P is detected with the sheet P placed flat and sandwiched between the sensor unit support 211 and the sheet loading table 230. Accordingly, the sheet information detecting sensor 210 does not detect deformed portions on the sheet P and detects correct sheet information of the sheet P, and therefore performance of precise discrimination of sheet types is prevented from being degraded.

Further, given detection intervals (sampling periods) of sheet information detected by the sheet information detecting sensor 210 of the sheet discriminator 220 may be optionally set and/or changed by a service representative or a user.

By so doing, as the detection intervals of sheet information of the sheet P become shorter (as the sampling periods of sheet information of the sheet P are more accelerated), more detection results can be obtained at the same amount of movement of the sheet discriminator 220 with respect to the sheet P. As a result, more precise discrimination of the sheet P can be performed. In addition to the effect that the sheet discriminator 220 can obtain a large amount of detection results, a space used for an operator to perform the above-described detection of information of the sheet P can be reduced, and therefore the sheet discriminator 220 can encourage and achieve space saving.

Further, the sheet discriminator 220 according to this example may be connected with the image forming apparatus 2 included in the image forming system 1 via the communication cable 60, so that the image forming conditions can be changed based on the detection results of the sheet P obtained by the sheet discriminator 220.

As a result, when a new image forming operation is performed, the time and effort of a user to manually input the image forming conditions corresponding to the sheet P used for the image forming operation can be saved. At the same time, human error such as incorrect setting can be avoided.

What is claimed is:
1. A sheet information detecting device comprising:
a sheet loader for receiving a sheet;
an information detector configured to detect information of the sheet loaded on the sheet loader, the information detector including
a light emitter configured to emit light to a surface of the sheet and to an interior of the sheet, and
a light receiver to receive the emitted light; and
the information detector configured to detect the information of the sheet with the sheet being inserted in the sheet loader,
wherein the light receiver of the information detector includes multiple light receivers, and
wherein the multiple light receivers include at least a transmission light receiver configured to receive light emitted from the light emitter and transmitted through the sheet.
2. The sheet information detecting device according to claim 1, further comprising:
a housing body having an opening and including at least the sheet loader and the information detector,
wherein the information detector is configured to detect the information of the sheet by inserting the sheet in the sheet loader via the opening and by sliding the sheet with respect to the housing body.
3. The sheet information detecting device according to claim 1, further comprising a support to support the sheet inserted to the sheet loader,
wherein the support is disposed at the housing body, and
wherein the information detector is configured to detect the information of the sheet by sliding the housing body with respect to the sheet supported by the support.
4. The sheet information detecting device according to claim 1, wherein the information detector is disposed facing the sheet loader.
5. The sheet information detecting device according to claim 4, further comprising a biasing member configured to bias the sheet loader toward the information detector.

6. The sheet information detecting device according to claim 1, wherein the information detector is disposed above the sheet loader.

7. The sheet information detecting device according to claim 1,
wherein the multiple light receivers include a specular reflection light receiver configured to receive specular reflection light emitted from the light emitter and reflected on the sheet and a diffused reflection light receiver to receive diffused reflection light emitted from the light emitter and reflected on the sheet.

8. The sheet information detecting device according to claim 1,
wherein the multiple light receivers include at least a reflected polarized light component receiver configured to receive component of diffused light reflected by the sheet.

9. The sheet information detecting device according to claim 1, further comprising;
an adjuster configured to adjust approach and separation of the information detector with respect to the sheet.

10. The sheet information detecting device according to claim 1, wherein detection intervals of sheet information detected by the information detector are optionally changed.

11. The sheet information detecting device according to claim 1, further comprising:
a communicator disposed between the sheet information detecting device and an image forming apparatus configured to communicate with each other.

12. A sheet discriminator comprising:
a sheet information detecting device according to claim 1; and
a sheet distinguisher configured to distinguish a type of the sheet based on the light detected from the surface and light detected from the interior of the sheet detected by the information detector, the information detector configured to detect the information of the sheet with the sheet being inserted between the sheet loader and the information detector,
the sheet distinguisher distinguishing the sheet based on detection results obtained at multiple points of the sheet by the information detector.

13. A sheet discriminator comprising:
a sheet information detecting device according to claim 1; and
a sheet distinguisher configured to distinguish a type of the sheet based on the light detected from the surface and light detected from the interior of the sheet detected by the information detector, the information detector configured to detect the information of the sheet with the sheet being inserted between the sheet loader and the information detector,
the sheet distinguisher discriminating a thickness of the sheet based on detection results obtained by the information detector.

14. A sheet discriminator comprising:
a sheet information detecting device according to claim 1; and
a sheet distinguisher configured to distinguish a type of the sheet based on the light detected from the surface and light detected from the interior of the sheet detected by the information detector, the information detector configured to detect the information of the sheet with the sheet being inserted between the sheet loader and the information detector,
the sheet distinguisher discriminating surface properties of the sheet based on detection results obtained by the information detector.

15. A sheet discriminator comprising:
a sheet information detecting device according to claim 1; and
a sheet distinguisher configured to distinguish a type of the sheet based on the light detected from the surface and light detected from the interior of the sheet detected by the information detector, the information detector configured to detect the information of the sheet with the sheet being inserted between the sheet loader and the information detector,
the sheet distinguisher configured to discriminate a brand of the sheet based on detection results obtained by the information detector.

16. The sheet discriminator according to claim 12, wherein the sheet discriminator is disposed outside an image forming apparatus.

17. An image forming apparatus comprising:
a sheet discriminator according to claim 12; and
an image forming part configured to form an image on the sheet.

18. The image forming apparatus according to claim 17, wherein the sheet discriminator is disposed outside an image forming apparatus.

19. The image forming apparatus according to claim 18, wherein an image forming condition is changed based on detection results of the sheet obtained by the sheet discriminator.

20. The sheet information detecting device as recited in claim 1, wherein the transmission light receiver is positioned on a side of the sheet opposite the light emitter.

* * * * *